(12) United States Patent
Elia et al.

(10) Patent No.: US 11,399,731 B2
(45) Date of Patent: Aug. 2, 2022

(54) SYSTEMS AND METHODS FOR IMPEDANCE TOMOGRAPHY OF A BODY PART OF A PATIENT

(71) Applicant: ZBra Care Ltd., Tel-Aviv (IL)

(72) Inventors: Liron Elia, Kiryat-Ata (IL); Gavriel J. Iddan, Haifa (IL); Nir Lilach, Kfar Yehoshua (IL)

(73) Assignee: ZBra Care Ltd., Tel-Aviv (IL)

( * ) Notice: Subject to any disclaimer, the term of this patent is extended or adjusted under 35 U.S.C. 154(b) by 0 days.

(21) Appl. No.: 17/290,838

(22) PCT Filed: Nov. 3, 2019

(86) PCT No.: PCT/IL2019/051199
§ 371 (c)(1),
(2) Date: May 3, 2021

(87) PCT Pub. No.: WO2020/089918
PCT Pub. Date: May 7, 2020

(65) Prior Publication Data
US 2022/0000385 A1 Jan. 6, 2022

Related U.S. Application Data

(60) Provisional application No. 62/755,429, filed on Nov. 3, 2018.

(51) Int. Cl.
*A61B 5/0536* (2021.01)
*A61B 5/25* (2021.01)
*A61B 5/00* (2006.01)

(52) U.S. Cl.
CPC .............. *A61B 5/0536* (2013.01); *A61B 5/25* (2021.01); *A61B 5/6804* (2013.01); *A61B 5/7267* (2013.01)

(58) Field of Classification Search
CPC ....... A61B 5/0536; A61B 5/25; A61B 5/6804; A61B 5/7267; A61B 1/041; A61B 5/073;
(Continued)

(56) References Cited

U.S. PATENT DOCUMENTS 8,886,291 B2   11/2014   Hartov et al.
2014/0018681 A1   1/2014   Chang et al.

FOREIGN PATENT DOCUMENTS

DE   102016114611   2/2018
GB   2530355   3/2016
(Continued)

OTHER PUBLICATIONS

International Preliminary Report on Patentability dated May 14, 2021 From the International Bureau of WIPO Re. Application No. PCT/IL2019/051199. (9 Pages).
(Continued)

*Primary Examiner* — Patrick Fernandes

(57) ABSTRACT

There is provided a system for mixed imaging modalities including impedance based analysis of a body portion of a patient, comprising: multi conductor busbar(s), each connected to a controller and at least two of multiple sensing components, a controller arranged to: iteratively perform: sequentially activate as a current source, a first sensing component previously un-used as the current source in earlier iterations, sequentially activating as a current sink, a second sensing component previously un-used as the current sink in earlier iterations, obtain surface voltages, by sequentially activating each of the other sensing components as a respective voltage sensor, and obtaining a respective voltage reading while alternating current is transmitted between the first and second sensing components, wherein the voltages and current obtained for each pair of first and second sensing
(Continued)

component of each iteration are provided for computation of a 3D dataset of 3D impedance values of the body portion.

22 Claims, 42 Drawing Sheets

(58) Field of Classification Search
CPC .. A61B 5/0031; A61B 5/4836; A61J 15/0084; A61M 2210/1053; A61M 2205/3317; A61M 2230/65; G16H 40/63; G16H 50/30; G16H 20/40; G16H 50/20; H03H 9/0509; H03H 9/0585; H03H 9/54; H03H 9/64
See application file for complete search history.

(56) References Cited

FOREIGN PATENT DOCUMENTS

| WO | WO 2009/042637 | 4/2009 |
| WO | WO 2015/083958 | 6/2015 |
| WO | WO 2020/089918 | 5/2020 |

OTHER PUBLICATIONS

International Search Report and the Written Opinion dated Feb. 23, 2020 From the International Searching Authority Re. Application No. PCT/IL2019/051199. (12 Pages).

Akhtari-Zavare et al. "Electrical Impedance Tomography as a Primary Screening Technique for Breast Cancer Detection", Asian Pacific Journal of Cancer, 16(14): 5595-5597, 2015.
Grossi et al. "Electrical Impedance Spectroscopy (EIS) for Biological Analysis and Food Characterization: A Review", Journal of Sensors and Sensor Systems, 6(2): 303-325, Published Online Aug. 28, 2017.
Prasad et al. "Breast Imaging Using 3D Electrical Impedence Tomography", Biomedical Papers of the Medical Faculty of the University Palacky, Olomouc, Czech Republic, 152(1): 151-154, Jun. 2008.
Romsauerova et al. "Multi-Frequency Electrical Impedance Tomography (EIT) of the Adult Human Head: Initial Findings in Brain Tumours, Arteriovenous Malformations and Chronic Stroke, Development of an Analysis Method and Calibration", Psychological Measurement, 27: S147-S161. Published Online Apr. 20, 2006.
Wagenaar "Electrical Impedance Tomography in 3D: Characterization and Evaluation", A Thesis Submitted to the Faculty of Graduate and Postdoctoral Affairs in Partial Fulfillment of the Requirements for the Degree of Master of Applied Science in Biomedical Engineering, Department of Systems and Computing engineering, Carleton University, Ottawa, Ontario, Canada, p. 1-130, 2015.
Yusof "Electrical Impedance Tomography (EIT) in Breast Cancer Screening", Health Technology Assessment Section, Medical Development Division, Ministry of Health Malaysia, p. 1-6, Apr. 2009.
Supplementary Partial European Search Report and the Provisional Opinion dated Dec. 7, 2021 From the European Patent Office Re. Application No. 19877589.2 (15 Pages).
Supplementary European Search Report and the European Search Opinion Dated Mar. 14, 2022 From the European Patent Office Re. Application No. 19877589.2. (15 Pages).

Fig. 1: bra system ("electro bra")

Measurements $r_t$ for t's from 1 to T generate a vector:

$$r = [r_1, r_2, \ldots, r_t, \ldots, r_T]$$

$$r_t = \sum_{i}^{k} R_{n,m} \qquad m = \frac{l-j}{k-i} n$$

It can be written as a matrix vector operation as follows:

$$R = [R_{1,1} \ldots R_{1,M}, R_{2,1} \ldots R_{2,1}, \ldots R_{2,M}, \ldots \ldots R_{N,1} \ldots R_{N,M}]$$

$$\begin{bmatrix} r_1 \\ \cdot \\ \cdot \\ \cdot \\ \cdot \\ r_t \end{bmatrix} = \begin{bmatrix} 0 & 1 & 1 & 0 & 1 & 1 & 0 \\ \cdot & & & & & & \cdot \\ \cdot & & & A & & & \cdot \\ \cdot & & & & & & \cdot \\ 1 & 1 & 0 & 1 & 1 & 0 & 1 \end{bmatrix} \begin{bmatrix} R_{1,1} \\ \cdot \\ \cdot \\ \cdot \\ \cdot \\ R_{N,M} \end{bmatrix}$$

The matrix A is the digital equivalent of the well known Radon transformation that form the basis of CT.
In short:
$$r = A\,R$$

FIG. 22

The solution vector R rearranged as a impedance matrix

| $R_{11}$ | | | | | $R_{1N}$ |
| --- | --- | --- | --- | --- | --- |
| | | | | | |
| | | | $R_{3,4}$ | | |
| | | | | | |
| $R_{M1}$ | | | | | $R_{MN}$ |

FIG. 23

SYSTEMS AND METHODS FOR IMPEDANCE TOMOGRAPHY OF A BODY PART OF A PATIENT

RELATED APPLICATIONS

This application is a National Phase of PCT Patent Application No. PCT/IL2019/051199 having an international filing date of Nov. 3, 2019, which claims the benefit of priority under 35 USC § 119(e) of U.S. Provisional Patent Application No. 62/755,429 filed on Nov. 3, 2018. The contents of the above applications are all incorporated by reference as if fully set forth heren in their entirety.

FIELD AND BACKGROUND OF THE INVENTION

The present invention, in some embodiments thereof, relates to impedance tomography and, more specifically, but not exclusively, to systems and methods for impedance tomography of a body part of a patient.

Medical imaging is performed, for example, for screening for cancer. Due to the abundance of breast cancer, screening tests are recommended to catch breast cancer at its early stages. A simple low cost and comfortable early examination method as a first step in diagnostics is sought. The common approach, x-ray mammography followed by ultra-sonic scan, a fairly effective procedure, is done by an expert physician in a clinic. The exam is uncomfortable and utilizes ionizing radiation. The x-ray and/or ultrasound procedure requires the patient to visit a clinic and is very uncomfortable since it requires painful squeezing of the examined breast, in addition the x-ray is an ionizing radiation which is by itself a suspected carcinogenic source. Electrical impedance tomography is being explored as a screening option for breast cancer.

SUMMARY OF THE INVENTION

According to a first aspect, a system for mixed imaging modalities including impedance based analysis of a body portion of a patient, comprises: at least one multi conductor busbar, each bus bar connected to a controller and at least two of a plurality of sensing components, a controller arranged to: iteratively perform: sequentially activate as a current source, a first sensing component previously un-used as the current source in earlier iterations, sequentially activating as a current sink, a second sensing component previously un-used as the current sink in earlier iterations, obtain a plurality of surface voltages, by sequentially activating each of the other sensing components as a respective voltage sensor, and obtaining a respective voltage reading while alternating current (AC) is transmitted between the first and second sensing components, wherein the plurality of voltages and current obtained for each pair of first and second sensing component of each iteration are provided for computation of a three dimensional (3D) dataset of 3D impedance values of the body portion, provided for analysis thereof.

According to a second aspect, a method of an impedance based analysis of a body portion of a patient, comprises: providing at least one busbar, each bus bar connected to a controller and at least two of a plurality of sensing components, iteratively performing: sequentially activating as a pair of current electrodes at a time, pair of current electrodes, wherein a plurality of voltages and current obtained for each pair of current electrodes of each iteration are provided for computation of a three dimensional (3D) dataset of impedance values of the body portion, provided for analysis thereof.

In a further implementation form of the first, and second aspects, the controller performs sequentially activating of a certain sensing component of the plurality of sensing components by transmitting a unique address associated with the certain sensing component on the at least one busbar.

In a further implementation form of the first, and second aspects, each respective sensing component includes: (i) an address decoder that is activated when a unique address associated with the respective sensing component is transmitted over the respective busbar connected to the respective sensing component, (ii) at least one electrode for contacting tissue, (iii) at least one switch that connects the at least one electrode to the respective busbar when the address decoder is activated by the unique address, and (iv) an assignment mode decoder that receives instructions from the respective busbar for selectively operating the at least one electrode as a current source, as a current sink, or as a voltage sensor, when the address decoder is activated by the unique address.

In a further implementation form of the first, and second aspects, each respective sensing component further includes an amplifier for amplifying the voltage reading obtained by the at least one electrode when the assignment mode decoder operates the at least one electrode as the voltage sensor.

In a further implementation form of the first, and second aspects, the at least busbar includes the following busbar components: a transmit current component for transmission of current for operating a respective assigned sensing components as a current source, a receive current components operating as current mode, a ground component denoting ground, at least one voltage component for transmission of sensed voltage from at least one respective voltage sensor, an address component for transmission of the unique address, and a clock component.

In a further implementation form of the first, and second aspects, further comprising a pressure-surface coupled to the plurality of sensing components, the pressure-surface includes an urging element set to urge the plurality of sensing components for contacting the body portion at a uniform pressure within a tolerance In a further implementation form of the first, and second aspects, the urging surface comprises a lumen for inflation with a fluid, wherein when in use, when the fluid, is inserted into the lumen, the lumen expands, and a suction tube for creating a vacuum between the body portion and an inner surface of an arrangement supporting the sensing components, for improving contact between electrodes of the sensing components and the body portion.

In a further implementation form of the first, and second aspects, further comprising at least one hardware processor executing a code for: computing a computational model of the 3D dataset of impedance values, matching the obtained voltages and currents obtained for each pair of current source and current sink for a plurality of iterations to computed boundary values obtained by the computational model including Laplace's equation incorporating distributed conductivity, and iteratively adjusting the computational model including the conductivity distribution until the obtained voltages and currents match the computed boundary values within an error range.

In a further implementation form of the first, and second aspects, an initial set of conductivity distribution values of the computational model of the 3D dataset is obtained by the controller sequentially activating a respective pair of current source and current sink from the plurality of sensing components, and obtaining voltage readings from the respective pair of current source and current sink while current is flowing between the respective pair.

In a further implementation form of the first, and second aspects, the analysis of the body portion, by conductivity distribution mapping for tissue anomaly observation, is for planning treatment of the patient.

In a further implementation form of the first, and second aspects, the body portion comprises one or two breasts, and the plurality of sensing components are arranged as a bra for cupping the one or two breasts.

In a further implementation form of the first, and second aspects, the body portion comprises a head, and the plurality of sensing components are arranged as a hat for cupping the head.

In a further implementation form of the first, and second aspects, further comprising a plurality of support elements arranged for contacting and at least partially cupping the body portion of the patient, wherein the at least one busbar and the plurality of sensing components are coupled to the at least one support element.

In a further implementation form of the first, and second aspects, the plurality of support elements are arranged in a partial or full ring arrangement for encompassing at least a respective region of the body portion of the patient.

In a further implementation form of the first, and second aspects, each respective support element of the plurality of support elements includes a single respective busbar for connecting to at least two sensing components coupled to the respective support element and for connecting to a single main busbar connected to the controller.

In a further implementation form of the first, and second aspects, the plurality of support elements are arranged as a plurality of parallel elongated strips having variable diameters corresponding to a diameter of the body portion contacting each respective support element when the cup arrangement is cupping the body portion when in use, wherein the plurality of sensing components are arranged along a longitudinal axis of the elongated strip.

In a further implementation form of the first, and second aspects, the plurality of support elements are arranged as extensions from a common region of the cup arrangement, wherein each extension curves out from the common region.

In a further implementation form of the first, and second aspects, sensing components are automatically sequentially activated in a predefined cascade by circuitry that automatically triggers activation of a subsequently connected sensing component when a current sensing component is selected, such that selection of a first sensing component in a sequence of connected sensing components automatically triggers the sequential independent activation of a next sensing component in the sequence.

In a further implementation form of the first, and second aspects, further comprising at least one hardware processor executing a code for generating an impedance based intra-body 3D conductivity mapping image of the body portion from the 3D dataset.

In a further implementation form of the first, and second aspects, further comprising code for segmenting tissue indicative of likelihood of malignancy depicted in the 3D image.

In a further implementation form of the first, and second aspects, the segmenting is performed by a machine learning model trained on a training dataset of a plurality of 3D conductivity images obtained from a plurality of sample patients.

In a further implementation form of the first, and second aspects, the controller activates each pair of the first and second sensing components and the other sensing components as the respective voltage sensor three times for obtaining a plurality of sets of voltage readings each at a different frequency of the current, for designating a respective color channel for each one of the plurality of sets of voltage readings corresponding to a different frequency, and wherein the 3D image is generated in color using the respective color channels.

In a further implementation form of the first, and second aspects, the controller is further designed to activate at least one of the plurality of sensing components in ultrasound mode for intra-body ultrasonic/conductivity multi mode imaging of the body portion.

In a further implementation form of the first, and second aspects, the controller is further designed to sequentially activate in ultrasound mode, at least some of the sensing components, obtain respective ultrasound measurement, and provide a plurality of ultrasound measurements for generating at least one of: a 3D ultrasound intra-body image of the body portion, and conductivity mapping.

In a further implementation form of the first, and second aspects, further comprising at least one hardware processor executing a code for correlating the 3D dataset of impedance values with the plurality of ultrasound measurements, and generating a correlated 3D image of the body portion from the correlated conductivity values and ultrasound measurements.

In a further implementation form of the first, and second aspects, at least a subset of the plurality of sensing components are designed further operate in ultrasound mode, by each including a tissue electrode for contacting the body portion, a second electrode in parallel with the tissue electrode, and an ultrasonic element sandwiched between the tissue electrode and the second electrode, wherein the tissue element is selectively activated as the current source, the current sink or the voltage sensor, and in an ultrasound mode the tissue electrode, the ultrasound element, and the second electrode are activated as an ultrasound transducer.

In a further implementation form of the first, and second aspects, further comprising a respective second sensor of a plurality of second sensors located in proximity to at least some of the plurality of sensing components, each bus bar connected to at least two of the plurality of second sensors, wherein the controller is further arranged to sequentially independently activate at a time, each respective second sensor, for collecting a plurality of second sensor measurements for generating a 3D image of the body portion based on the second sensor measurements.

In a further implementation form of the first, and second aspects, the second sensor comprises an infra-red (IR) sensor.

In a further implementation form of the first, and second aspects, at least one of: (i) the at least one multi conductor busbar includes a master busbar connected to each one of a plurality of branching sub-busbars each connected to a substantially circular arrangement of sensing components of a plurality of nested circular arrangements of sensing components, (ii) a single continuous busbar with a staggered designed, wherein a plurality of nested circular arrangements of sensing components are connected to one another and to the single continuous busbar by connector components included within the single continuous busbar, and (iii) a single continuous busbar arranged as a spiral connecting sensing components arranged in a spiral.

In a further implementation form of the first, and second aspects, a plurality of electrodes are arranged along a long axis of each support element of a plurality of support elements, each of the plurality of electrodes including a respective individual conductor connected to a main busbar connector designed to connect to the at least one multi conductor busbar, wherein addressing circuitry and switching circuitry for sequential activation of the plurality of electrodes is located in association with the main busbar connector, which the plurality of support elements are arranged in a fan arrangement designed for being shaped into a cup like arrangement for cupping the body portion.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 22 depicts a matrix representation of vectors of impedance measurements obtained as described with reference to FIG. 21, in accordance with some embodiments of the present invention;

FIG. 23 is a schematic depicting a solution vector denoted R (e.g., as in FIG. 22) rearranged as an impedance matrix representing a 3D dataset, in accordance with some embodiments of the present invention;

DESCRIPTION OF SPECIFIC EMBODIMENTS OF THE INVENTION

Figure 1:
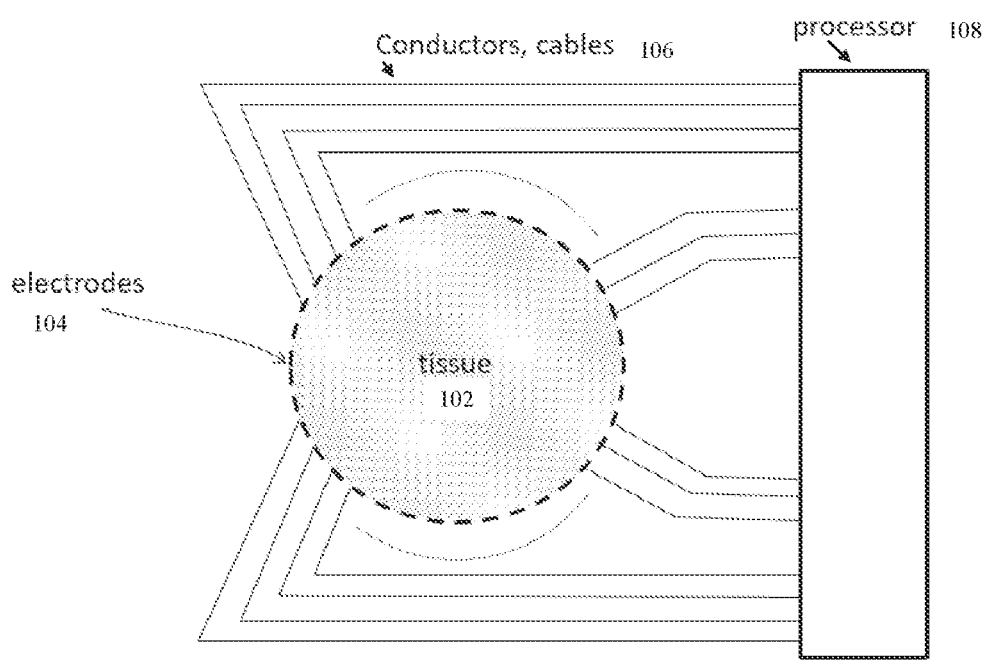
FIG. 1 is a schematic of impedance measurements of a tissue by multiple electrodes based on existing methods, where each electrode is independently connected to its own dedicated conductor (e.g., pair of cables), where all of the conductors are connected to a processor for analysis of the collected impedance measurement, to help understand the technical problem addressed by at least some embodiments of the present invention.

As used herein, the term "malignancy", used for example in relation to detection of an indication of malignancy in the 3D dataset described herein, may sometimes be interchanged with the term "anomaly", for example, an indication of an anomaly is detected in the 3D dataset. The anomaly may be indicative of a malignancy and/or other medical problem (e.g., intracranial bleeding).

As used herein, the term sensing component may sometimes be interchanged with the term electrode and/or current electrode. Sometimes, the term electrode or current electrode refers to the electrode component of the sensing component.

As used herein, sometimes the term 3D dataset of impedance values may be interchanged with the term 3D conductivity mapping.

An aspect of some embodiments of the present invention relates to systems, methods, an apparatus, and/or code instructions (e.g., stored on a memory and executable by hardware processor(s)) for generating a three dimensional (3D) dataset of impedance values of a body portion of a patient, for performing an impedance based analysis of the body portion, for example, for detection of an indication of malignancy within the tissue of the body portion. One or more multi conductor busbars (also referred to herein as busbar) are provided. Each busbar is connected to two or more sensing components. Each sensing component may be accessed using a common busbar via a respective unique address, optionally by transmission of signals on the common busbar indicative of the respective unique address which are decoded by an address decoder associated with each sensing component. The busbar(s) are connected to a controller. The controller sequentially activates sensing components in a selected operating mode, optionally by transmission of signals and an associated unique address of each sensing component of the sequence on the busbar(s).

The controller may iteratively and sequentially activate one selected component as a current source, and then activate another selected component as a current sink. Sensing components may be activated and operated individually and/or as pairs. During each iteration, another sensing component previously un-used as the current source in earlier iterations is selected as the current source, and another sensing component previously un-used as the current sink in earlier iterations is selected as the current sink. When current (alternating current (AC) and/or direct current (DC)) is passing between the pair of sensing components (i.e., current source and current sink), the controller may sequentially activate each of the other sensing components (i.e., that are not currently acting as the current source and current sink) as a respective voltage sensor, and obtain a respective voltage reading. The controller obtains, at each iterations, a dataset of multiple voltage readings (i.e., from each sensing component) and the current obtained passed between the pair of sensing components (i.e., current source and current sink) selected for the respective iteration. The multiple datasets may be combined and/or computed to obtain the 3D dataset of 3D impedance values of the body portion. A 3D image of the body portion, depicting the internal tissue of the body portion, may be computed and/or presented based on the 3D dataset of impedance values. The 3D image and/or the 3D dataset may be analyzed, for example, for detection and/or localization of an indication of malignancy within the body portion, optionally serving as a screening tool. The patient may be diagnosed according to the analysis, and/or treatment of the patient may be planned according to the analysis, for example, additional imaging of the patient may be performed using other modalities (e.g., mammography, ultrasound), a biopsy may be performed, surgery may be performed, chemotherapy may be administered, radiation therapy may be administered, and/or a watch and wait approach may be selected (e.g., perform another impedance mapping procedure in 6 months).

Optionally, each respective sensing component includes: (i) an address decoder that is activated when a unique address associated with the respective sensing component is transmitted over the respective busbar connected to the respective sensing component; (ii) at least one electrode for contacting tissue; (iii) at least one switch that connects the at least one electrode to the respective busbar when the adder decoder is activated by the unique address; and (iv) an assignment mode decoder that receives instructions from the respective busbar for selectively operating the at least one electrode as a current source, as a current sink, or as a voltage sensor, when the address decoder is activated by the unique address.

Optionally, a computational model of the 3D dataset of impedance values is provided. The voltages and currents obtained for each pair of sensing components (i.e., current source and current sink) during the multiple iterations, are compared to computed boundary values obtained by the computational model, which may include Laplace's equations incorporating distributed conductivity. The actual measurements are performed on the outer surface of the body portion while the actual values within the interior of the body portion cannot be directly measured but are inferred based on the surface measured values. The outer surface of the body portion represents the boundary values of the computational model. Values of parameters of the computational model, optionally the conductivity distribution, are iteratively adjusted until the obtained voltages and currents match the computed boundary values within an error range. An initial set of conductivity distribution (e.g., impedance values) of the computational model of the 3D dataset may be obtained by the controller sequentially activating a respective pair of current source and current sink sensing components, and obtaining voltage readings from the respective pair of current source and current sink while current is flowing between the respective pair (i.e., without obtaining voltage readings from other sensing components that are not passing current during the respective iteration). The initial set of conductivity distribution (e.g., impedance values) improves accuracy of the computational model when the computational model is adjusted based on surface (e.g., of the skin) voltage values measured by sensing components (e.g., all sensing components) when a selected pair of sensing components are applying a current.

At least some implementations of the systems, methods, apparatus, and/or code instructions described herein relate to the technical problem of high resolution 3D impedance mapping of a 3D body part, for example, generating 3D impedance maps of a breast and/or head of a patient. By performing a tomographic reconstruction of a 3D impedance dataset (e.g., matrix), a 3D impedance map of the tissue denoting anomalies (e.g., lesions, malignancy) may be generated. The technical problem is addressed by the controller that iteratively sequentially activates and operates a pair of sensing components that apply a current between them. The controller performs the activation and operation by transmitting an address indicative of the selected sensing component(s) and optionally operation instructions on a multi conductor busbar that is connected to multiple different sensing components. While the current is applied, other sensing components (i.e., that are not currently applying the current) are sequentially activated and operated as voltage sensors for obtaining surface voltage readings (e.g., at the skin). At each iteration, a new pair of sensing components are selected, where each of the selected sensing components has not served the same function in the past (e.g., current source and/or current sink). For each new pair, a set of voltage measurements is obtained. A computational model of the 3D dataset of impedance values is computed, by matching the obtained voltages and currents obtained for each pair of current source and current sink for the iterations to computed boundary values obtained by the computational model, optionally mainly Laplace's equation incorporating the distributed conductivity, and iteratively adjusting the computational model including the conductivity distribution until the obtained voltages and currents match the computed boundary values within an error range. An initial set of conductivity distribution values of the computational model of the 3D dataset is obtained by the controller sequentially activating a respective pair of current source and current sink from the sensing components, and obtaining voltage readings from the respective pair of current source and current sink while current is flowing between the respective pair. The architecture of the busbar connected to multiple addressable sensing components reduces the size and/or number of communication conductors for communication between the controller and the sensing components. The adjustment of the conductivity distribution by matching to measured voltages collected by multiple other sensing components while current is flowing between a pair of sensing components increases accuracy of the 3D impedance map computed from the conductivity distribution. The initial conductivity distribution and/or adjustment of the conductivity distribution by matching to measured voltages increases computational efficiency, by reducing computational time for convergence, for example, in comparison to using a random and/or uniform value for the initial conductivity distribution and/or when matching to measured voltages (while current is applied) is not used.

At least some implementations of the systems, methods, apparatus, and/or code instructions described herein relate to the technical problem of impedance tomography for imaging of a body portion of a patient, for example, breast imaging such as to detect breast cancer, and/or brain imaging such as to detect brain cancer. Impedance mapping may be used, for example, to distinguish healthy tissue from tumor inflicted tissue. The problem may relate to detection of small abnormalities in tissues (e.g., small tumors), which requires a large number of electrodes (e.g., on the order of hundreds or thousands, for example, about 100-1000, or about 1000-3000 or other ranges) to obtain high resolution imaging, for high accuracy and/or medical validity, for example, objects having a dimension of about 0.5 centimeters (cm), or about 0.2 cm. Existing systems and methods, where each electrode is connected to its own conductor, require a very large number of conductors to obtain desired high resolution imaging (e.g., for small tumors), which is impracticable, and therefore a practical product has never matured.

At least some implementations of the systems, methods, apparatus, and/or code instructions described herein improve the technical field of impedance tomography for imaging of a body portion of a patient, for example, breast imaging such as to detect breast cancer, and/or brain imaging such as to detect brain cancer. The improvement is obtained by the sensing components that perform impedance measurements that are independently individually serially addressable via a relatively small number of conductors (e.g., busses), for example, less than 10 conductors. In some implementations, one conductor connects all of the sensing components. Alternatively, one conductor connects the groups of multiple, with multiple conducts optionally implemented. The use of the small number of conductors enables close positioning of the sensing components, which provides for high resolution imaging. In contrast, existing systems and methods use individual conductors per electrode (e.g., a dedicated pair of transmission wires for each electrode), which involves a large amount of cables, which is cumbersome, increases complexity, increases room for error, and/or reduces accuracy due to interference between conducting wires. Each electrode may be individually connected to a common processor, which is highly impractical, especially when a large number of electrodes are used. The resolution of the image is limited by the ability to closely place electrodes in order to leave room for the wires. The high resolution 3D dataset of impedance values is further obtained by at least some implementations of the systems, methods, apparatus, and/or code instructions described herein, that iteratively activate a pair of sensing components for current, and while current is being applied between the pair, iteratively activate each one of the other sensing components to sense voltage. The obtained data is used to compute a highly accurate 3D dataset of impedance values, which may be used to reconstruct a 3D image and/or analyzed to detect anomalies within the tissue.

At least some implementations of the systems, methods, apparatus, and/or code instructions described herein relate to treatment of a patient, for example, for screening for breast cancer and/or brain cancer. The device described herein, which includes impedance electrodes housed in a bra-like structure and/or a hat-like structure and a controller that iteratively activates pairs of sensing components for current and other sensing components for voltage while current is being transmitted by an active pair, may be used to collect data for generation of a 3D impedance dataset of the breast(s) and/or head which may be analyzed to detect malignancy and/or used to create a 3D image. The data collection procedure may be carried out at home by the examinee. The wearable bra-like and/or hat-like device is designed to be comfortable, does not require administration of x-ray radiation, and/or may be performed at a relatively low cost. The data may be transmitted to a remote server and/or cloud for image construction and/or analysis (e.g., diagnosis). The analysis such as diagnosis may be automatically performed by code. The results may be reviewed by an expert via the internet. The patient may be instructed for further treatment accordingly, for example, to perform another impedance collection session now, another session in the future (e.g., in a year), go for traditional mammographic and/or ultrasonic imaging and/or CT and/or MRI imaging, biopsy, surgery, chemotherapy, and/or other treatments.

Reference is now made to FIG. 1, which is a schematic of impedance measurements of a tissue 102 by multiple electrodes 104 based on existing methods, where each electrode 104 is independently connected to its own dedicated conductor (e.g., pair of cables) 106, where all of the conductors 106 are connected to a processor 108 for analysis of the collected impedance measurement, to help understand the technical problem addressed by at least some embodiments of the present invention. The large number of conductors (i.e., at least one for each electrode) limits the number of electrodes that may be implemented, which reduces measurement resolution, and has other disadvantages, as described herein. In contrast, as described herein, at least some implementations of the systems, methods, apparatus, and/or code instructions described herein provide a relatively small number of conducts connect between the processor and a large number of electrodes, providing for high resolution imaging of tissue.

At least some implementations of the systems, methods, apparatus, and/or code instructions described herein relate to the technical problem of increasing accuracy of detection and/or localization of a region of interest in the computed image, for example, a region likely depicting malignancy. At least some implementations of the systems, methods, apparatus, and/or code instructions described herein improve the technology of medical imaging, by increasing accuracy of detection and/or localization of a region of interest in the computed image. The technical solution and/or technical improvement is based on the sensor component architecture, busbar connection, and controller activation described herein. In some implementations, the same sensor component may be operated in impedance measurement mode for obtaining impedance measurements, and operated in ultrasound mode for obtaining ultrasound measurements. The same sensor component may be addressed using the same assigned address, optionally using the same busbar which is also connected to multiple other sensor components each having a respective unique address. In other implementations, two or more sensor components which are co-located (e.g., next to each other) are assigned the same unique address but independently operated to obtain different imaging modalities, for example, impedance measurement and/or ultrasound measurement and/or infrared (IR) measurement. The sensor components having the same address may be selected and/or operated using the same busbar which is also connected to multiple sensor components each having a respective unique addresses.

The following probabilistic analysis is presented to help illustrate the increase in accuracy from the multiple mode imaging described herein, where sensors of each modality share a common address (e.g., impedance measurements and ultrasound using the same sensor component having a single common address, and/or sensor component and IR sensor that are in proximity to one another and which may share the same address). For 4 different tomographic sensors of the same tissue, include: bioimpedance, x-ray, ultrasound (ULS) and infrared:

The probability of detection by impedance is denoted $p_1$. The probability of missing the detection by impedance is denoted $1-p_1$. The probability of detection by x-ray is denoted $p_2$. The probability of missing by x-ray is denoted $1-p_2$. The probability of detection by ultrasound is denoted $p_3$. The probability of missing by ULS is denoted $1-p_3$. The probability of detection by IR is denoted $p_4$. The probability of missing by IR is denoted $1-p_4$.

The probability of detection of the combined four fused sensor system (assuming independence) is given by the following mathematical relationships:

$$p_{fussion} = p_1 + (1-p_1) \cdot p_2 + [1-(1-p_1) \cdot p_2] \cdot p_3 + \{1-[1-(1-p_1) \cdot p_2] \cdot p_3\} \cdot p_4$$

or:

$$p_{fussion} = \Sigma_1^4 p_i - \Sigma_1^3 p_i \cdot p_{i+1} + \Sigma_1^2 p_i \cdot p_{i+1} \cdot p_{i+2} - \Pi_1^4 p_i$$

Assuming equal detection probability of the 4 sensors $p_i=0.8$ for I=1, 2, 3, 4, the probability of detection by 2 sensors p(2)=0.8+(1−0.8)0.8=0.96=96%,
the probability of detection by 3 sensors p(3)=0.96+(1−0.96)0.8=0.992=99.2%,
the probability of detection by 4 sensors p(4)=0.992+(1−0.992)0.8=0.9984=99.84%.

The above computation indicates that an optimal accuracy is obtained with two or three sensors, while combining more than 3 sensors may yield a marginal advantage.

At least some implementations of the systems, methods, apparatus, and/or code instructions described herein relate to the technical problem of creating the 3D impedance based image based on a desired current directly travelling within the body of the patient between the current injection electrode and the current collector electrode, while reducing or eliminating effects of other undesired indirectly travelling currents, which may interfere with the desired current. Additional details of the technical problem are described herein. The technical problem is solved by gating and/or solving Laplace equations, as described herein.

At least some implementations of the systems, methods, apparatus, and/or code instructions described herein relate to the technical problem of increasing accuracy of the measured impedance values. Contact pressure between the electrodes (of the sensing components) and tissue may affect the impedance measurement. In general, the higher the contact pressure the lower the measured impedance. Non-uniform pressured of the electrodes applied to the skin may result in measurement errors. A pressure-element (also referred to as a pressure surface) described herein, provides uniform contact force of the sensing components to the tissue of the patient may increase accuracy of the generated 3D impedance dataset by reducing variations in measurements resulting from variations in contact pressure, which contribute to impedance mapping error.

At least some implementations of the systems, methods, apparatus, and/or code instructions described herein relate to the technical problem of improving depth of 3D impedance imaging of body portions. For example, existing systems use electrodes that are arranged along a plane, which limits depth of imaging, to about 4 centimeters or less. In contrast, the 3D cupping arrangement described herein may improve the generated 3D impedance map, by positioning the sensing components in a non-planar arrangement, on an outer surface of the volume of the body portion. The currents transmitted between selected current sinks and sources may traverse within the interior of the body portions. The resulting 3D impedance map may depict deeper regions of the interior of the body, for example, above 4 centimeters, or being able to fully image the entire volume of target tissue.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
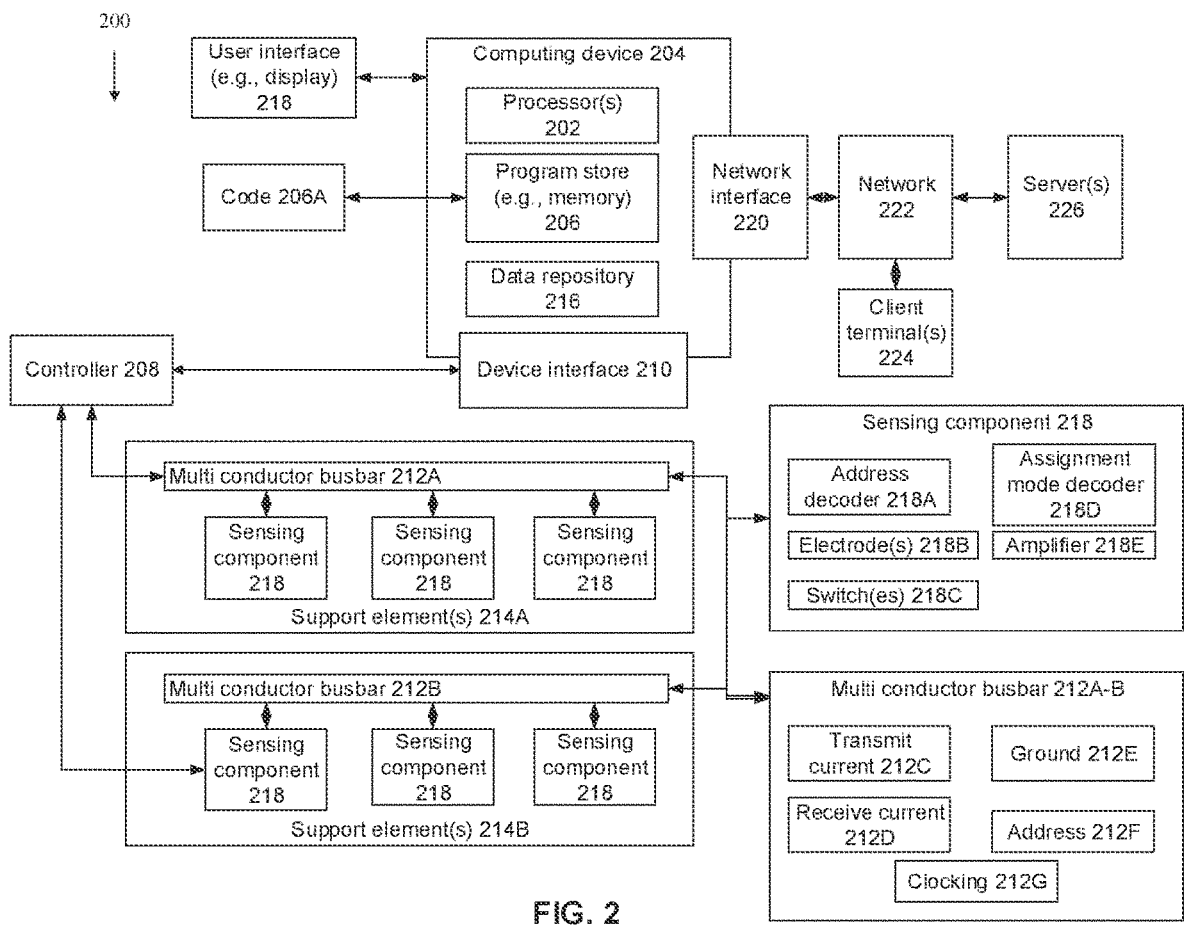
FIG. 2 is a schematic of a system for generating a 3D dataset of 3D impedance values of a body portion of a patient by sequentially independently activating sensing components connected to a busbar which is connected to multiple other sensing components, in accordance with some embodiments of the present invention.
Figure 3A:
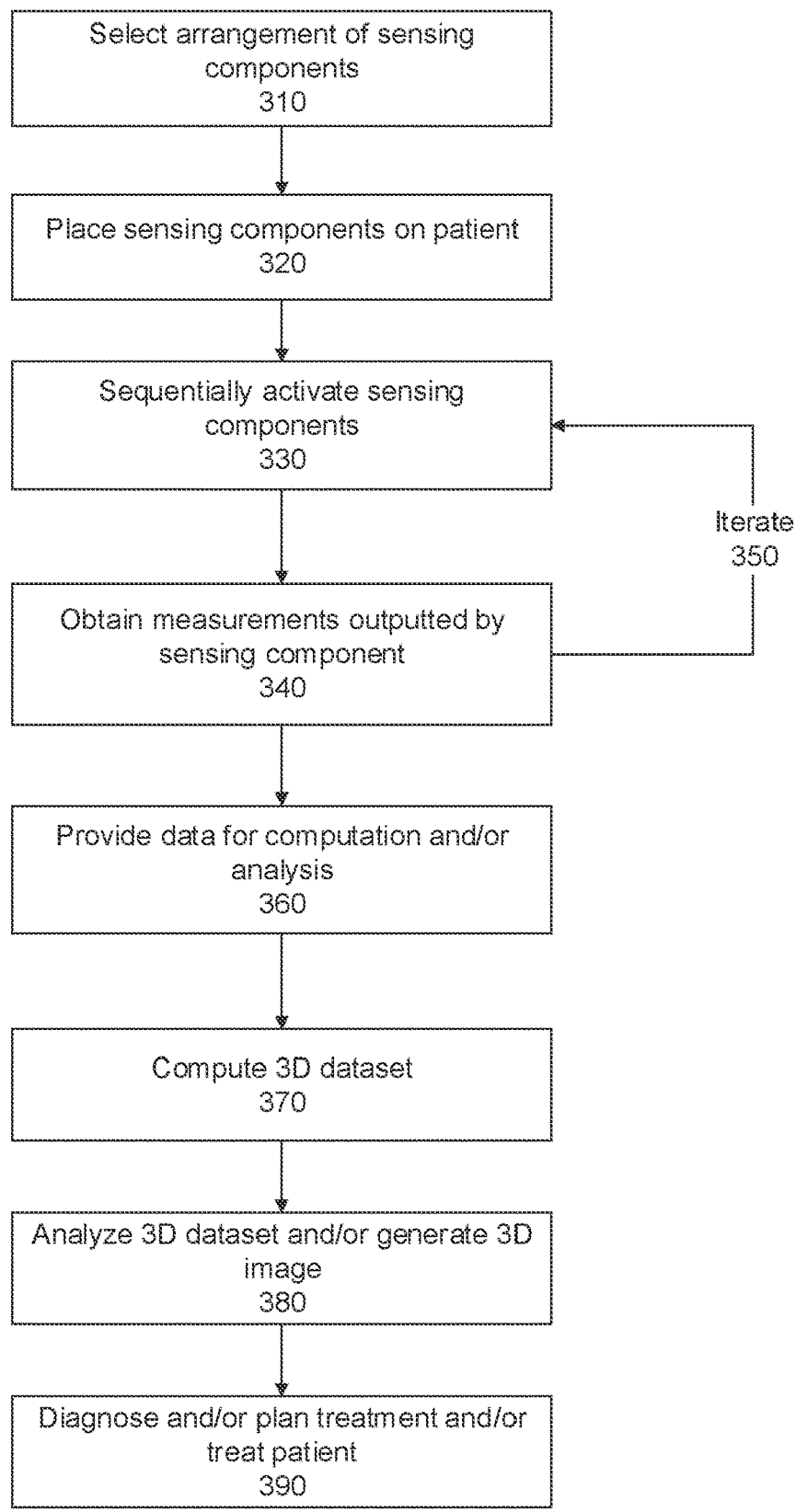
FIG. 3A is a flowchart of a computer implemented method for generating a 3D dataset of 3D impedance values of a body portion of a patient by sequentially independently activating sensing components connected to a busbar which is connected to multiple other sensing components, in accordance with some embodiments of the present invention.
Figure 3B:
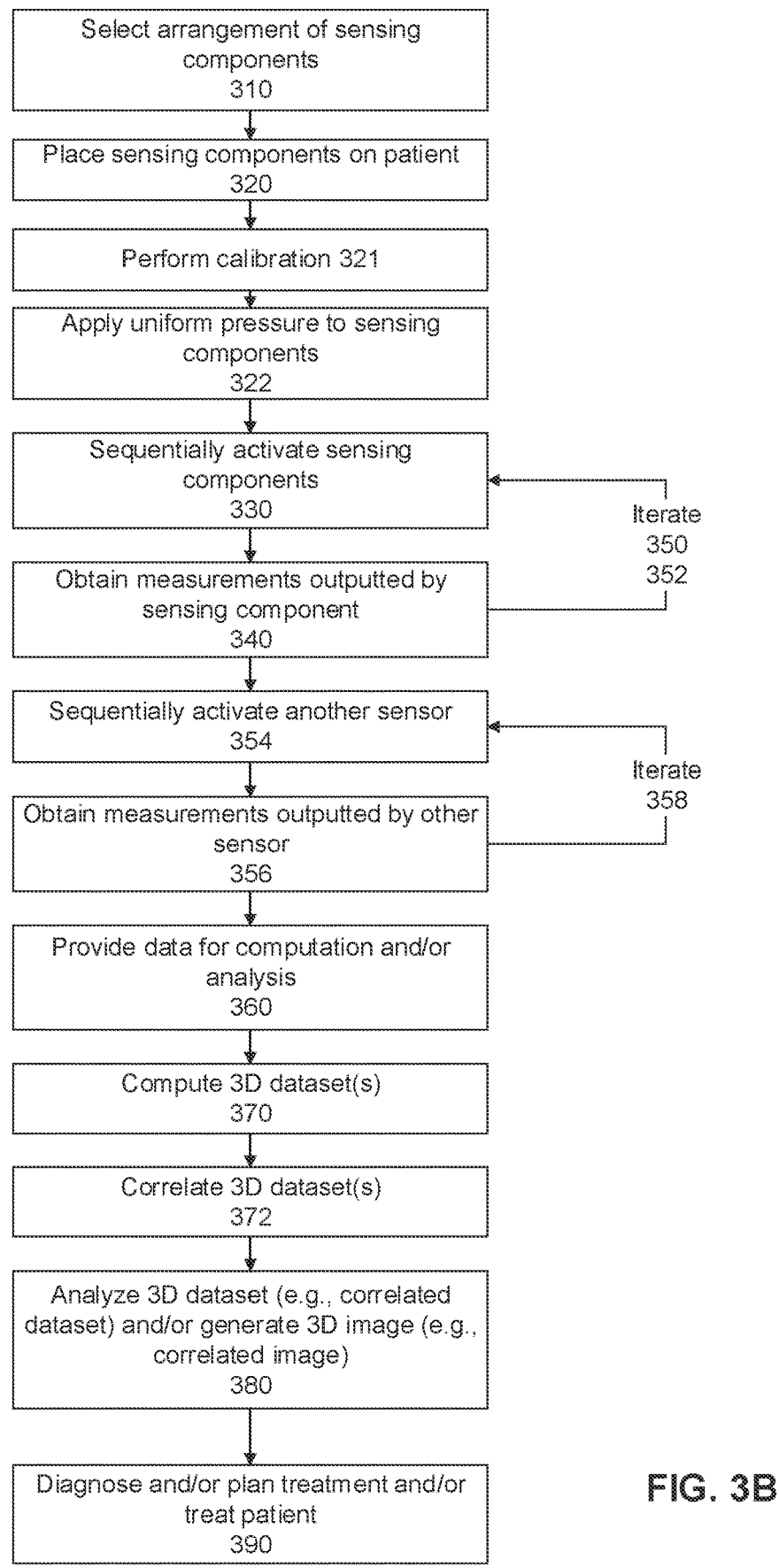
FIG. 3B is a flowchart based on FIG. 3A that includes additional optional features, in accordance with some embodiments of the present invention.

Reference is now made to FIG. 2, which is a schematic of a system 200 for generating a 3D dataset of 3D impedance values of a body portion of a patient by sequentially independently activating sensing components connected to a busbar which is connected to multiple other sensing components, in accordance with some embodiments of the present invention. Reference is also made to FIG. 3A, which is a flowchart of a computer implemented method for generating a 3D dataset of 3D impedance values of a body portion of a patient by sequentially independently activating sensing components connected to a busbar which is connected to multiple other sensing components, in accordance with some embodiments of the present invention. Reference is also made to FIG. 3B, which is a flowchart based on FIG. 3A that includes additional optional features, in accordance with some embodiments of the present invention. One or more acts of the method described with reference to FIGS. 3A-B may be implemented by components of system 200, as described herein, for example, by a processor(s) 202 of a computing device 204 executing code instructions 206A stored in a program store (e.g., memory) 206.

Computing device 204 is in electrical communication with a controller 208 (e.g., combined transmitter and receiver components, or separate transmitter and receiver components 208) that generates instructions for activation and/or operation of individual and/or pairs of sensing components 218 from a set of sensing components optionally of a common support element (e.g., 214A), where multiple sensing components 218 are connected to a multi conductor busbar (e.g., 212A). Each multi conductor busbar may be associated with a respective support element. There may be one multi conductor busbar, or multiple multi conductor busbars. Each busbar is connected to at least two sensing components (which are addressable over the same busbar as described herein) and to the controller. As used herein, the term busbar and multi connector busbar are interchangeable.

Controller 208 is designed to: iteratively perform: sequentially activate as a current source, a first sensing component previously un-used as the current source in earlier iterations, sequentially activating as a current sink, a second sensing component previously un-used as the current sink in earlier iterations, obtain a plurality of surface (e.g., skin) voltages, by sequentially activating each of the other sensing components as a respective voltage sensor, and obtaining a respective voltage reading while current (e.g., alternating current and/or direct current) is transmitted between the two sensing components.

Each respective sensing component includes one or more of the following sub-components (implemented in hardware such as circuitry and/or software such as code stored in a memory executed by a processor):

(i) an address decoder 218A that is activated when a unique address associated with the respective sensing component is transmitted over the respective busbar connected to the respective sensing component;

(ii) one or more electrodes 218B for contacting tissue, where the electrode(s) is designed to apply current, receive current, and/or perform voltage measurements;

(iii) one or more switches 218C that connects the electrode(s) to the respective busbar (e.g., to the respective conducting line of the multi conductor busbar) when the adder decoder is activated by the unique address; and (iv) an assignment mode decoder 218D that receives instructions from the respective busbar for selectively operating the at least one electrode as a current source, as a current sink, or as a voltage sensor, when the address decoder is activated by the unique address.

(v) an amplifier 218E for amplifying the voltage reading and/or current reading obtained by the electrode(s) when the assignment mode decoder operates the electrode(s) as the voltage sensor and/or current electrode.

The multi conductor busbar includes one or more of the following busbar components (e.g., conductors, such as conductor lines, or sub-busbars):

(i) a transmit current component 212C for transmission of current for operating a respective sensing component as a current source, (ii) a receive current component 212D for receiving current from a respective sensing component operating as a current sink, (iii) a ground component 212E denoting ground, at least one voltage component for transmission of sensed voltage from at least one respective voltage sensor, (iv) an address component 212F for transmission of the unique address. The address component may include a single conduction line, or multiple conduction lines, for example, one line for each of the addressing bits, and (v) a clocking component 212G for transmission of a clock signal.

It is noted that there may be multiple support elements, or a single support element, or no support elements. Two 214A-B are depicted as an example. Each support element may include the same or different number of sensing components 218 thereon. Each busbar (e.g., 212A) is connected to multiple sensing components 218 of the respective support element (e.g., 214A). Each busbar (e.g., 212A) may be implemented, for example, as a pair of wires, optionally one pair of wires.

Controller 208 may include a transceiver for injection of electrical signals to the selected pair of sensing components, and receiving a signal from the pair of sensing components, for example, the signal is injected into one sensing component of the selected pair of sensing components which acts as a transmitter and a measurement of the received signal by the other sensing component of the pair is performed. Computing device 204 generates instructions for operating controller 208, and/or receives data from controller 208, optionally via a device interface 210. Alternatively, computing device 204 and controller 208 are implemented as a single device and/or controller 208 is integrated within computing device 204, for example, as another hardware component and/or as code installed on computing device 204. When computing device 204 and controller 208 are integrated, device interface 210 may be, for example, an internal software interface.

Computing device 204 includes device interface 210 that provides electrical communication with one or more controllers 208. Device interface 210 may be implemented as, for example, a network interface card, a hardware interface card, a wireless interface, a short range wireless interface (e.g., blue tooth), a physical interface for connecting to a cable, a virtual interface implemented in software, communication software providing higher layers of connectivity (e.g., application programming interface (API), software development kit (SDK), and/or other implementations.

It is noted that an interface corresponding to device interface 210 may be associated with the support elements and/or with controller 208, for example, for wireless communication between the support elements and the computing device 204. For example, device interface 210 may provide communication between the controller 208 and sensing components 218, via the multi conductor busbar, for example, by a wireless communication channel.

Optionally, computing device 204 is implemented as hardware, for example, circuitry, an assembly of hardware components, an integrated circuit, and/or other architectures. Alternatively or additionally, computing device 204 may be implemented as, for example, a standalone unit, a hardware component, a client terminal, a server, a computing cloud, a mobile device, a desktop computer, a thin client, a Smartphone, a Tablet computer, a laptop computer, a wearable computer, glasses computer, and a watch computer. Computing device 204 may include locally stored software and/or hardware that perform one or more of the acts described with reference to FIG. 3A-B.

Processor(s) 202 of computing device 204 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 202 may include one or more processors (homogenous or heterogeneous), which may be arranged for parallel processing, as clusters and/or as one or more multi core processing units.

As used herein, the term processor may sometimes be interchanged with the term computing device.

Storage device (also known herein as a program store, e.g., a memory) 206 stores code instructions implementable by processor(s) 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Storage device 206 stores code instruction 206A that execute one or more acts of the method described with reference to FIG. 3A-B. Alternatively or additionally, one or more acts of the method described with reference to FIG. 3A-B are implemented in hardware.

Computing device 204 may include a data repository 216 for storing data, for example, the 3D dataset that stores the impedance measurements obtained from different sensing components for generation of the image of the body portion of the patient, and/or the generated images. Data repository 216 may be implemented as, for example, a memory, a local hard-drive, a removable storage unit, an optical disk, a storage device, and/or as a remote server and/or computing cloud (e.g., accessed via a network connection).

Computing device 204 includes and/or is in communication with a user interface 218 that includes a mechanism for a user to enter data (e.g., patient information) and/or view presented data (e.g., generated images). Exemplary user interfaces 218 include, for example, one or more of, a touchscreen, a display, a keyboard, a mouse, and voice activated software using speakers and microphone. External devices communicating with computing device 204 may be used as user interfaces 218, for example, a smartphone running an application may establish communication (e.g., cellular, network, short range wireless) with computing device 204 using a communication interface (e.g., network interface, cellular interface, short range wireless network interface).

Computing device 204 may include a network interface 220 for connecting to a network 222, for example, one or more of, a network interface card, a wireless interface to connect to a wireless network, a physical interface for connecting to a cable for network connectivity, a virtual interface implemented in software, network communication software providing higher layers of network connectivity, and/or other implementations.

Computing device 204 may communicate using network 222 (or another communication channel, such as through a direct link (e.g., cable, wireless) and/or indirect link (e.g., via an intermediary computing device such as a server, and/or via a storage device) for example, with client terminal(s) 224 and/or server(s) 226. For example, server(s) 226 may receive the data collected from the sensing components 218 by the controller 208, and generate the 3D dataset and/or image(s) of the body portion of the patient. Server(s) 226 may provide centralized computation services to multiple remote controllers 208 (and/or remote computing devices 204) for computing the 3D dataset and/or for computing the 3D image. Server(s) 226 may analyze the 3D dataset and/or the generated image, for example to detect an indication of malignancy, for example, by a machine learning model that is trained using data obtained from multiple sample patients (e.g., via respective remote computing devices 204 and/or controller 208). Client terminal(s) 224 may connect to server(s) 226 and/or computing device 204 over network 222. For example, the image computed by server(s) 226 using data collected by the computing device 204 is provided for presentation on a display of client terminal(s) 224. In another example, computing device 204 and/or server(s) 226 may obtain additional data of the patient, for example, imaging results obtained from other imaging modalities, and/or medical history data obtained from an electronic medical record of the patient. The additional data may be used to analyze the computed image of the body portion of the patient, for example, to improve accuracy of detecting malignancy.

Referring now back to FIG. 3A, at 310, an arrangement of the sensing components is selected, for example, according to the target body portion to be analyzed, for example, one or both breasts such as for detection of an indication of malignancy, and/or the head such as for detection of an indication of a clinical abnormality such as an indication of malignancy and/or bleeding.

Different sizes of arrangement may be available, for example, to fit breasts of different sizes and/or heads of different sizes.

The sensing components and/or busbar(s) may be coupled to one or more support elements, as described herein. The arrangement of the sensing components and/or support elements may be for contacting and/or at least partially cupping the body portion of the patient. The cupping arrangement may improve the generated 3D impedance map, by positioning the sensing components in a non-planar arrangement, on an outer surface of the volume of the body portion. The currents transmitted between selected current sinks and sources may traverse within the interior of the body portions. The resulting 3D impedance map may depict deeper regions of the interior of the body. For example, in contrast to existing planar arrangements of electrodes that are limited in ability to image deeper into tissues.

For example, when the body portion is one or both breasts of the target individual, the sensing components may be arranged as a bra for cupping the one or two breasts. In another example, when the body portion comprises a head, the sensing components may be arranged as a hat for cupping the head.

Optionally, each respective support component may include a single respective busbar for connecting to the multiple sensing components coupled to the respective support element and for connecting to a single main busbar connected to the controller.

Support elements may be manufactured as independent strips, which are connected into different structures, for example, forming bras of different sizes. Busbars of each strip may be connected to a main busbar, enabling modularity and/or customization of the arrangement according to the patient.

The sensing component and/or support element(s) may be arranged in a partial or full ring arrangement for encompassing at least a respective region of the body portion of the patient. Alternatively, or additionally, the sensing component and/or support elements are arranged as substantially parallel elongated strips having variable diameters corresponding to a diameter of the body portion contacting each respective support element when the cup arrangement is cupping the body portion when in use. The sensing components may be arranged along a longitudinal axis of the elongated strip. Alternatively or additionally, the sensing components and/or support elements are arranged as extensions (e.g., pizza slice shaped, rectangular shaped) from a common region of the cup arrangement. Each extension curves out from the common region.

The support elements may be made out, for example, flexible printed circuit board (FPCB) such as Kepton. Support elements and/or electrodes may be deposited on the FPCB (and/or other implementations of the support elements) using, for example, printing, spattering, and/or masking. The number of components (e.g., conduction lines) of each busbar is optionally 10 or less, or 7, or other numbers, as described herein.

Each support element may include multiple sensing components, for example, spaced and/or number selected according to a target imaging resolution. For example, 400 sensing components yield a resolution of about 5 millimeters (mm) on a 10×10 centimeter imaged tissue volume.

Each sensing component may be implemented as an application specific chip. The application specific chips may be mounted serially, and sequentially, spaced apart, on the support element, for example, using methods of SMT for manufacturing, such as automatically by a pick and place robot arm with soldering done by reflux.

Figure 4:
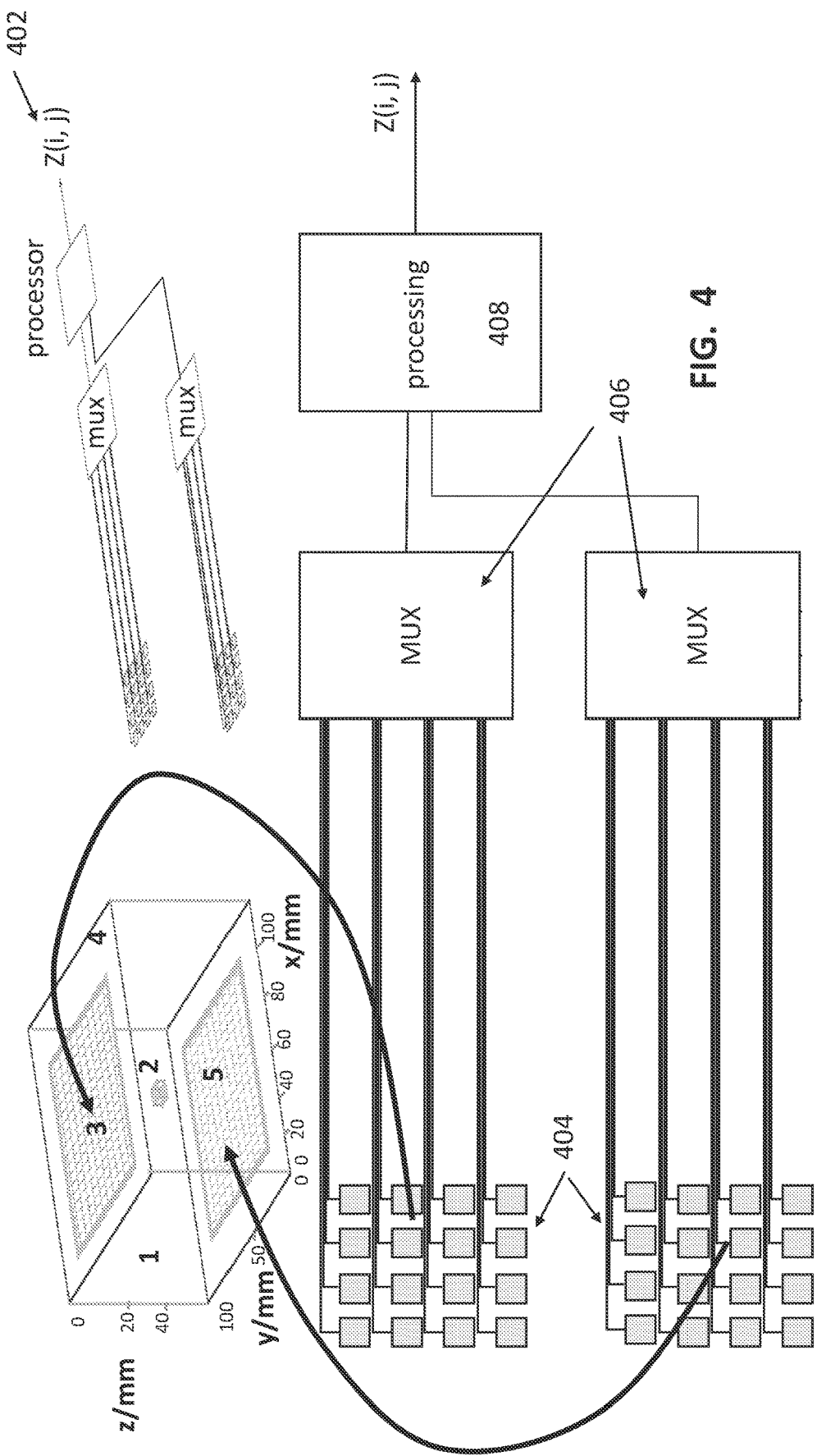
FIG. 4 is a schematic depicting an architecture of a parallel plate type breast tomography device for breast imaging, to help understand the technical problem addressed by at least some embodiments of the present invention.

Reference is now made to FIG. 4, which is a schematic depicting an architecture of a parallel plate type breast tomography device for breast imaging 402, to help understand the technical problem addressed by at least some embodiments of the present invention. Each one of electrodes 404 is connected by a dedicated cable to a mux 406 which feeds into a processor 408 for processing the signals for generation of the image. As described herein, the number of electrodes 404 and resolution of the resulting image is limited by the physical requirement to connect each electrode using its own cable connectors. For example, to obtain 1 mm imaging resolution, using an array of size 150 mm×150 mm, a total of 22500 conducts are required to connect to each one of the 22500 electrodes of the array.

Figure 5:
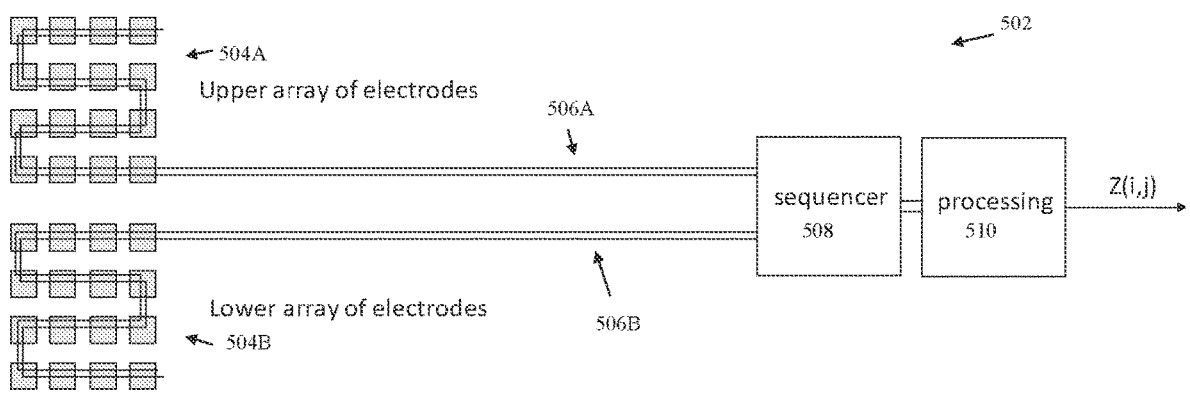
FIG. 5 is a schematic depicting an architecture where each set of multiple electrodes is connected to a common (e.g., single, such as one pair of wires of) multi conductor busbar, in accordance with some embodiments of the present invention.

Reference is now made to FIG. 5, which is a schematic depicting an architecture 502 where each set of multiple electrodes (e.g., upper array 504A and lower array 504B) is connected to a common (e.g., single, such as one pair of wires of) multi conductor busbar (respectively 506A and 506B), in accordance with some embodiments of the present invention. Architecture 502 which may be compared to device 402 of FIG. 4. Each connector 506A-B may connect to a sequencer 508 (which may perform serial addressing of the electrodes), which may further connect to a processor 510 for processing of the signals for generation of the image. The number of busbars may be independent of the number of electrodes, enabling high resolution imaging, for example, on the order of about 0.5 mm, or about 1 mm, or about 2 mm, or about 5 mm, or other smaller, intermediate or larger values. The total number of conductors of each busbar and/or the number of multi conductor busbars may be, for example, about 2, 4, 6, 8, 10, 12, or smaller or larger, which is significantly smaller than the number of conductors required when each electrode is connected to its own dedicated conductor (e.g., as depicted in FIG. 4)

Figure 6:
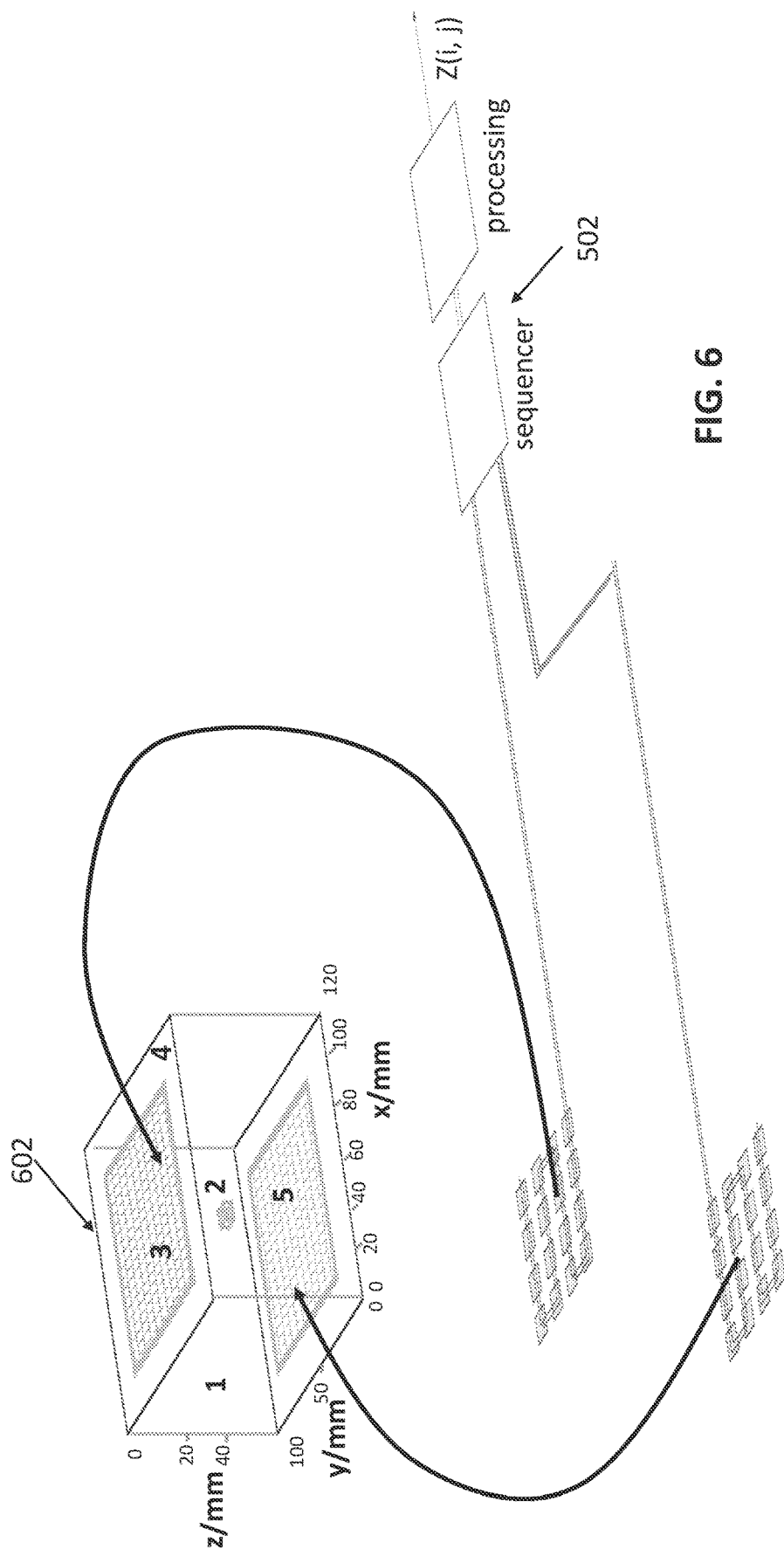
FIG. 6 is a schematic that depicts the architecture of FIG. 5 with respect to a two plate configuration which is common to x-ray mammography, in accordance with some embodiments of the present invention.

Reference is also made to FIG. 6, which depicts architecture 502 of FIG. 5 with respect to a two plate configuration 602 which is common to x-ray mammography, in accordance with some embodiments of the present invention.

Figure 7:
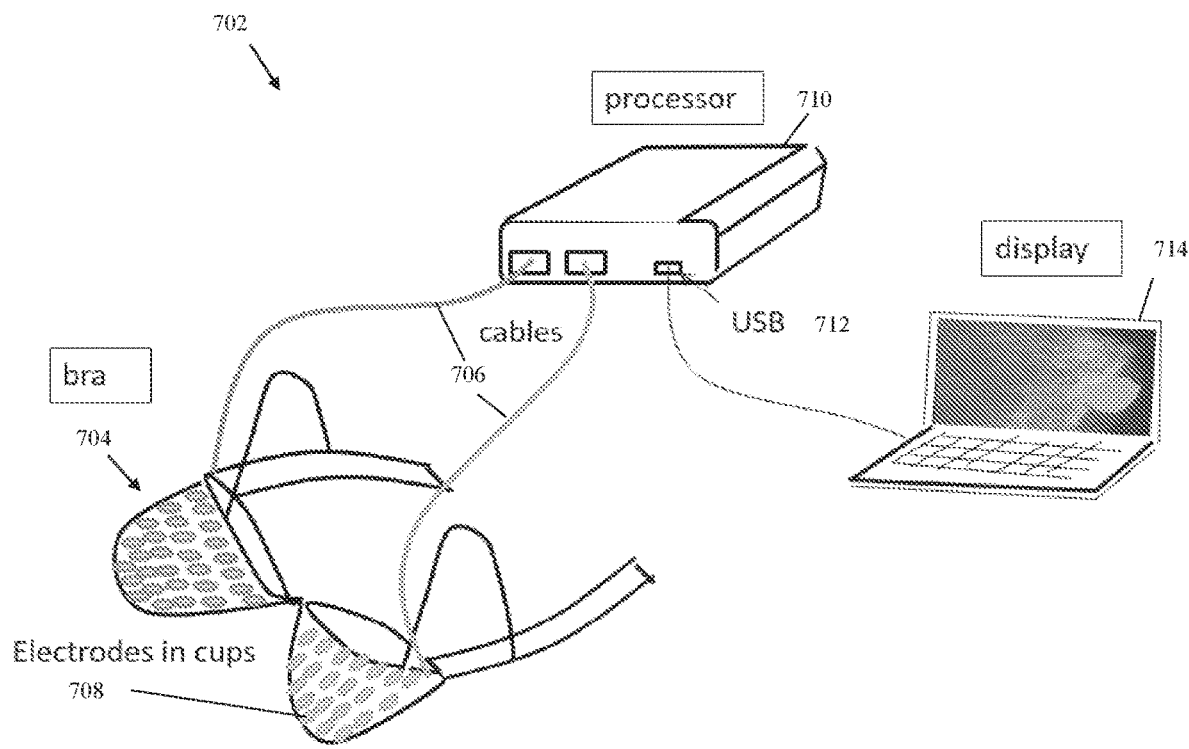
FIG. 7 is a schematic of an exemplary implementation of a system for collecting measurements for generating a 3D dataset of one or both breasts, optionally for detection of an indication of breast cancer, in accordance with some embodiments of the present invention.

Reference is now made to FIG. 7, which is a schematic of an exemplary implementation of a system 702 for collecting measurements for generating a 3D dataset of one or both breasts, optionally for detection of an indication of breast cancer, in accordance with some embodiments of the present invention. Sensing components 708 (that include electrodes) are housed in a bra shaped structure 704 designed to cup one or both breasts. In use, the sensing components 708 are positioned on the skin of the breast to obtain measurements from a non-planar surface of the breast, for generating a 3D dataset and/or 3D image, as described herein. Sensing components 708, which are individually addressable over a common busbar as described herein, are connected to a controller 710 (e.g., processor) via a small number of busbars 706, for example, two main busbars (that may include dedicated function component lines as described herein). A display 714 for presentation of the generated 3D image and/or analysis results may be connected to controller 710, for example via a USB port 712.

Figure 8:
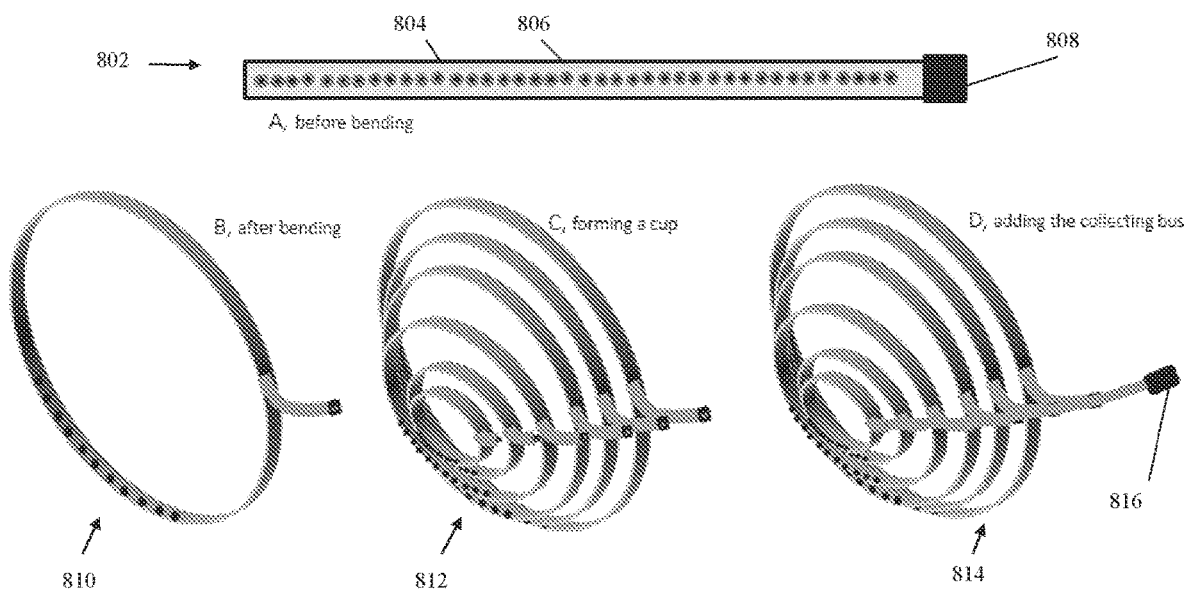
FIG. 8 is a schematic depicting an arrangement of sensing components for cupping a body portion, in accordance with some embodiments of the present invention.

Reference is now made to FIG. 8, which is a schematic depicting an arrangement of sensing components for cupping a body portion, in accordance with some embodiments of the present invention. Schematic 802 depicts a support element 804 having sensing components 806 thereon connected by a common busbar having a terminal connector 808. Schematic 810 depicts support element 804 with sensing components 806 thereon arranged in a circle and/or oval shape, for example, sized to fit a breast and/or head of a patient. Schematic 812 depicts multiple arrangements as shown in 810, each having a different radius, arranged for cupping a body portion, for example, a breast and/or head. Schematic 814 depicts a common main busbar 816 connected to terminal connectors 808 of the multiple arrangements of 812.

Figure 9:
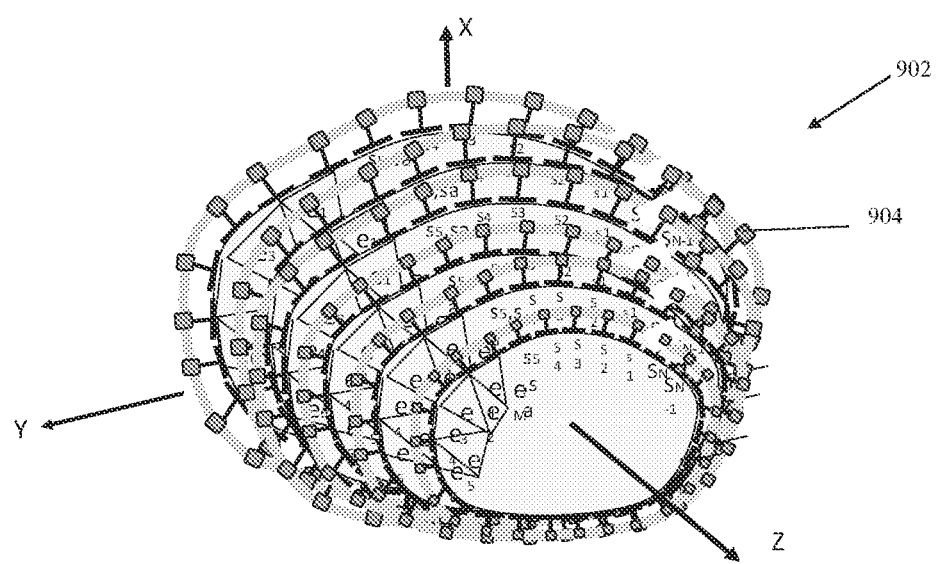
FIG. 9 is a schematic of a 3D arrangement of sensing components for obtaining measurements of a body portion for computation of a 3D dataset of impedance values, in accordance with some embodiments of the present invention.

Reference is now made to FIG. 9, which is a schematic of a 3D arrangement 902 of sensing components 904 for obtaining measurements of a body portion for computation of a 3D dataset of impedance values, in accordance with some embodiments of the present invention. 3D arrangement 902 is depicted for clarity without support elements.

Figure 10:
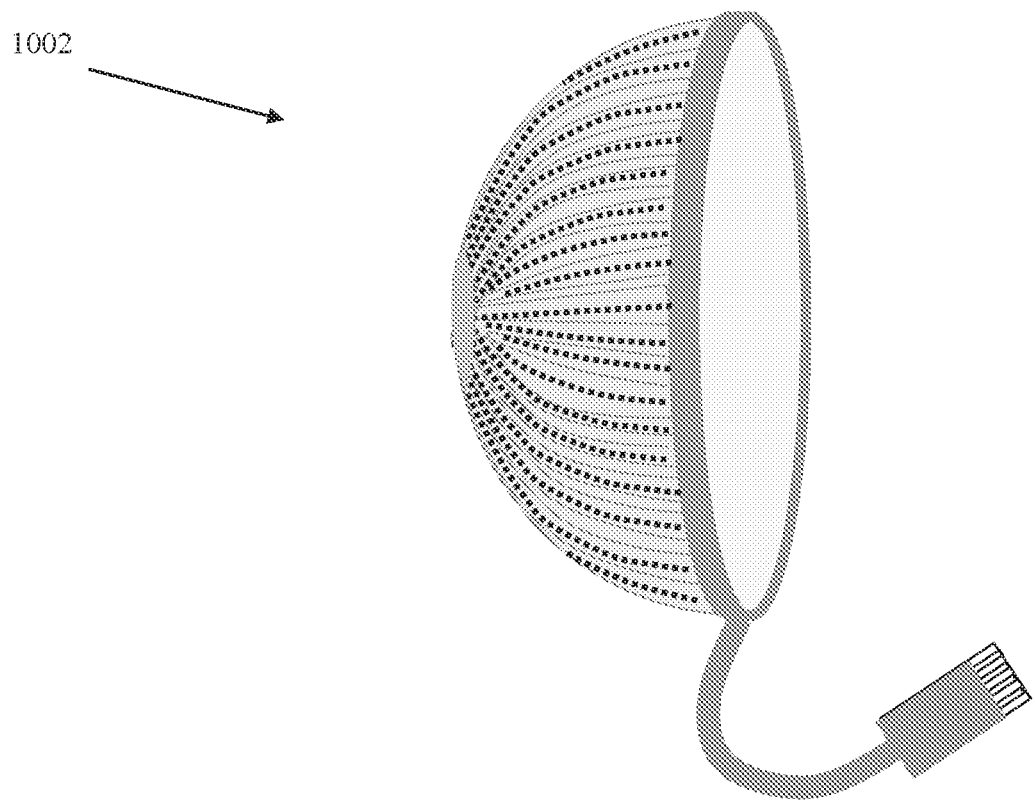
FIG. 10 is a schematic of an arrangement of sensing components coupled to support elements for cupping a body portion, in accordance with some embodiments of the present invention.

Reference is now made to FIG. 10, which is a schematic of an arrangement 1002 of sensing components coupled to support elements for cupping a body portion, in accordance with some embodiments of the present invention. For example, for cupping a breast or a head of a patient.

Figure 11:
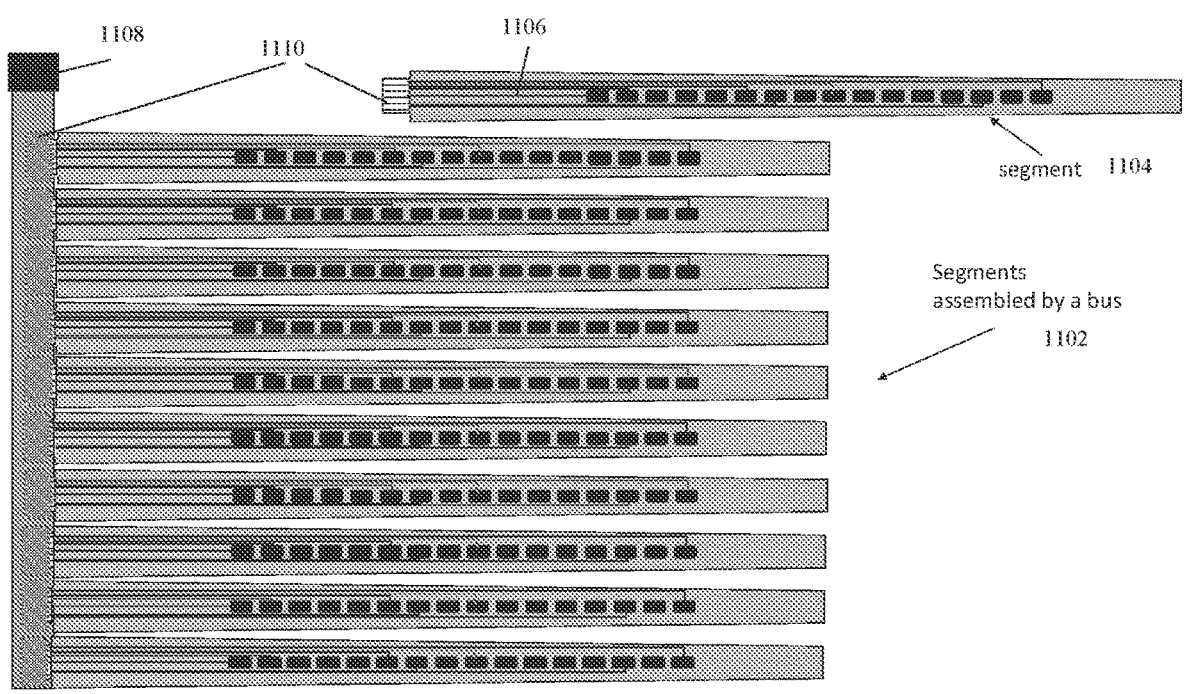
FIG. 11 is a schematic of an arrangement of multiple segments each including a set of sensing components, where each segment has its own respective common busbar attached to a single common main busbar connected to a controller (not shown), in accordance with some embodiments of the present invention.

Reference is now made to FIG. 11, which is a schematic of an arrangement 1102 of multiple segments 1104 each including a set of sensing components, where each segment 1104 has its own respective common busbar 1106 attached to a single common main busbar 1108 connected to a controller (not shown), in accordance with some embodiments of the present invention. Each segment 1104 may include a respective support element. The segments 1104 are connected to main busbar 1108, for example, by a respective connector 1110. Instructions (e.g., unique address, operation mode) flow from the controller, along main busbar 1108 to each one of the busbars 1106. Measurement data flows from a certain activated sensing component of a certain segment 1104 along the busbar 1106 of the segment to main bus bar 1108 and to the controller.

Figure 12:
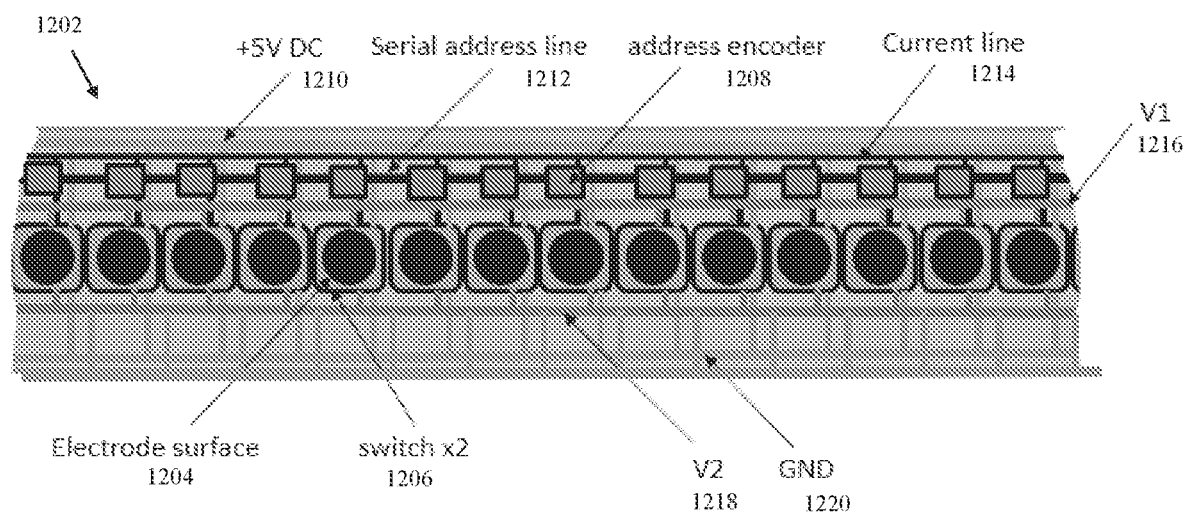
FIG. 12 is a schematic of a FPCB with coupled sensing components and busbar, in accordance with some embodiments of the present invention.

Reference is now made to FIG. 12, which is a schematic of a FPCB 1202 with coupled sensing components and busbar, in accordance with some embodiments of the present invention. Each sensing component may include one or more of the following components: electrode 1204, two switches 1206, and address encoder 1208. Each busbar may include one or more of the following components (e.g., lines): +5 V DC 1210, serial address line 1212, current line 1214, V1 line 1216, V2 line 1218 and ground (GND) line 1220.

Figure 39:
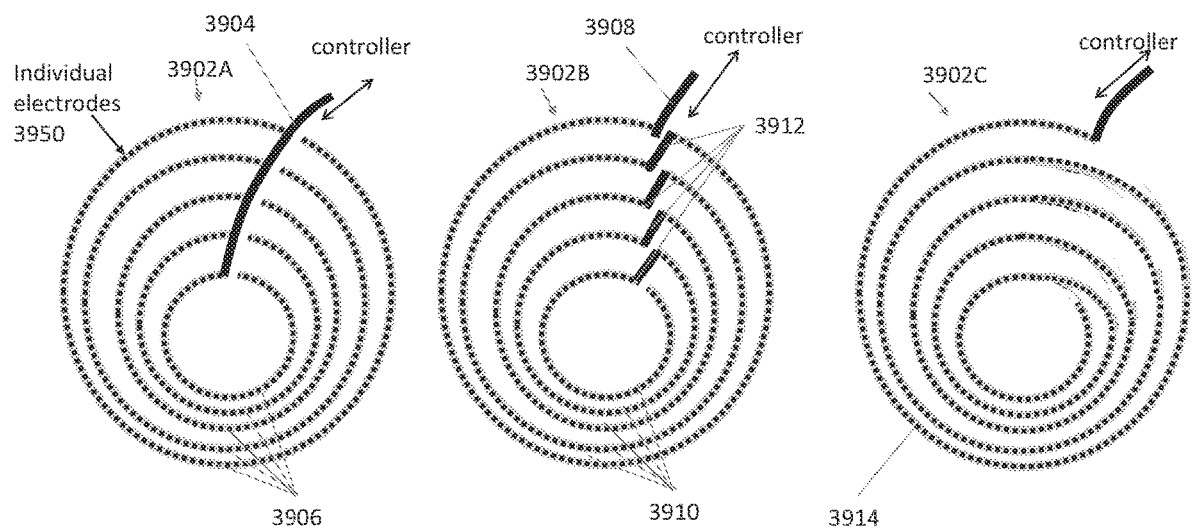
FIG. 39 is a schematic of exemplary architectures of curved (e.g., circular) busbars connecting an arrangement of the sensing components, in accordance with some embodiments of the present invention.

Reference is now made to FIG. 39, which is a schematic of exemplary architectures 3902A-C of curved (e.g., circular) busbars connecting an arrangement of the sensing components, in accordance with some embodiments of the present invention. The sensing components 3950 (also referred to as electrodes) may be arranged (e.g., via support elements) for cupping a substantially circular part of the body, for example, the head and/or breasts, as described herein. The busbars connect to the controller, as described herein.

Architecture 3902A includes a master busbar 3904 that connects to each one of multiple branching sub-busbars 3906. Each sub-busbar 3906 is connected to a circular (or arc, which may be most of a circle) arrangement of sensing components, which may be nested within each other (e.g., onion like).

Architecture 3902B includes a single continuous busbar 3908 with a staggered design, where layers of sensing components 3910 (e.g., arranged in a circle on support elements) are nested within one another (e.g., onion like), and connected to one another and to the single continuous busbar 3908 by connector components 3912 that are part of the continuous busbar 3908.

Architecture 3902C includes a single continuous busbar arranged as a spiral 3914. Sensing components (e.g., arranged in a circle on support elements) are arranged in a spiral connected to the spiral busbar 3914.

Figure 40:
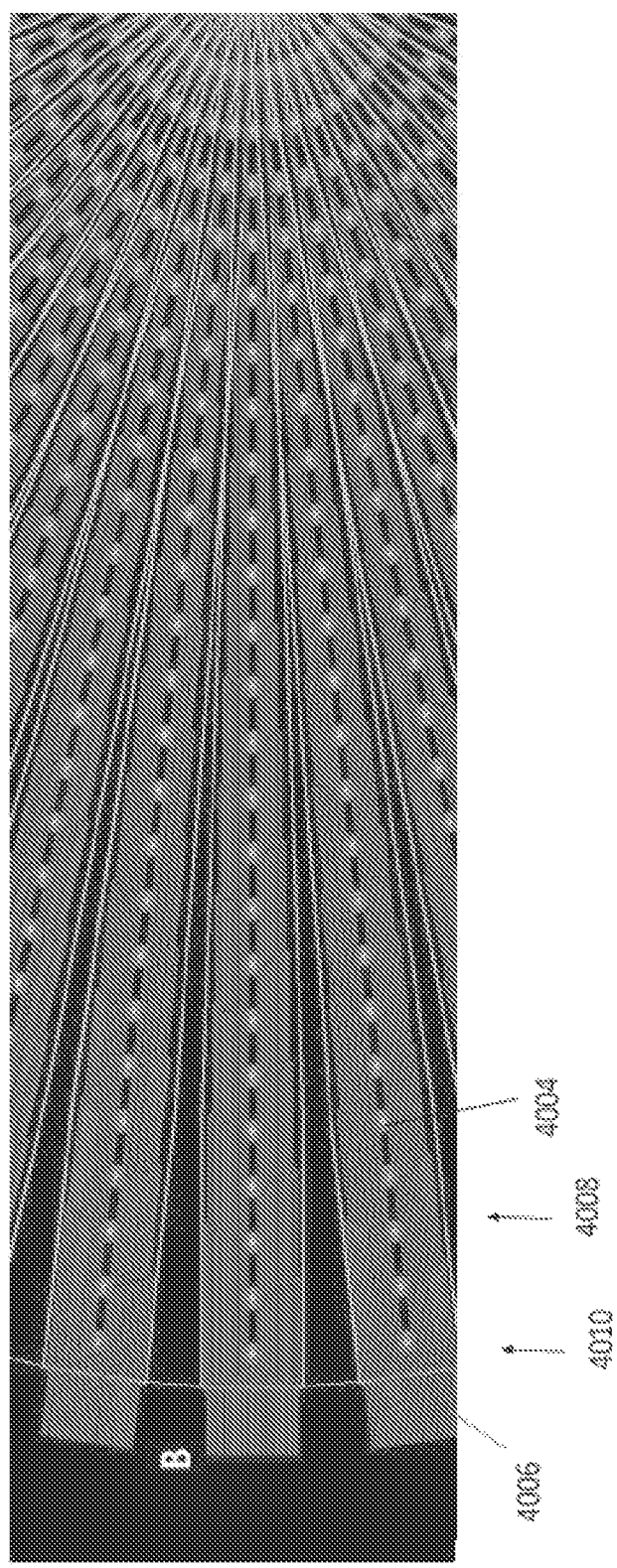
FIG. 40 includes schematics of exemplary arrangements of busbars, in accordance with some embodiments of the present invention.

Reference is now made to FIG. 40, which includes a schematic depicting an exemplary fan-shaped arrangement of busbars, in accordance with some embodiments of the present invention.

A support element (one support element 4008 is shown), for example, made from flexible PCB, to which multiple electrodes (one electrode 4004 is marked for clarity, where the number of electrodes is shown as 16, but not necessarily limiting, and may include fewer or greater number of electrodes) of corresponding sensing components are connected, where each electrode is separately connected by its own conductor (set of conductors 4010 for all 16 electrodes is marked) to a common busbar connector 4006 that connects to a common main busbar. Electrodes 4004 are spaced apart and arranged along a long axis of the support element.

A portion of a fan shaped arrangement of support elements 4008 is shown for clarity, where it is to be understood that a full fan shaped arrangement may be provided, or a partial arrangement may be provided. The common connector of each of the support elements in the fan shaped arrangement may be located towards the center of the fan shaped arrangement, or towards the exterior of the fan shaped arrangement. The fan shaped arrangement may be formed into a cup shaped arrangement for fitting to a body portion such as a head and/or breast, as described herein.

The electrode may be bunted on the sub-busbars. Each electrode 4004 may be connected via its own individual conductor to the main (e.g., master) busbar. The addressing and/or switch circuitry that activates and/or operates each electrode according to an address and instructions issued by the controller (as described herein) may be located at the busbar connector 4006. In such arrangement, the sensing component described herein is distributed between the electrode component of the sensing component and at the busbar connector which includes the addressing circuits, switches, and/or other sub-components as described herein. Alternatively, the addressing and/or switch circuitry is located at each electrode, as described herein.

A main busbar, optionally a single main busbar, connects to each one of the bus busbar connectors. Individual electrodes may be activated and/or operated based on an address and instructions provided by the controller over the main busbar, as described herein.

Referring now back to FIG. 3A, at 320, the sensing components are placed on the patient, for example, the bra arrangement is placed on the breasts, and/or the hat arrangement is placed on the head.

Optionally, the arrangement of sensing components include a busbar connector. The busbar connector may be plugged into a computing device acting as the controller, for example, plugged into a port (e.g., USB) of a mobile device. Alternatively, or additionally, the busbar connector is connected into a communication interface (e.g., mobile device, smartphone, router, wireless router) designed for network and/or wireless connection with the controller. For example, the controller may be located within a computing cloud and/or remote server. Alternatively or additionally, the controller is connected to the communication interface (or includes the communication interface) for communication with the computing cloud and/or remote server, where the data is sent for remote computation of the 3D dataset and/or remote analysis of the 3D data, for example, using a trained machine learning model (e.g., neural network).

At 330, the controller generates and transmits instructions for sequentially activating a certain sensing component for operating in a selected operation mode. Operation modes may include: current source, current sink, and voltage sensor. Additional operation modes may include operating as an ultrasound transceiver for ultrasonic imaging, and/or operating as an electrode (i.e., current source, sink, and/or voltage sensor), as described herein in additional detail.

Each measurement may include at least two sensing components acting as current transmitting electrodes for transmission of current therebetween.

The controller selected and/or activates the selected sensing component by transmitting a unique address associated with the certain sensing component on the busbar. The instructions include a unique address of the currently selected sensing component. The unique address may be transmitted over a common bus to which multiple sensing components are attached. The sensing component assigned the unique address implements the instructions. Other sensing components may listen to the busbar for their address and ignore the instructions when the address is not assigned to them. Addressing may be defined, for example, by a set of sequential and/or parallel signal bits transmitted over the busbar (e.g., over a dedicated line component of the busbar).

Optionally, a current source is first selected and activated from a certain sensing component. The selected sensing component may have been previously un-used as the current source in earlier iterations. Then, a current sink is selected and activated from another sensing component previously un-used as the current sink in earlier iterations. Optionally, each sensing component of the multiple sensing components is operated one time as a current sink, and/or one time as a current source. It is noted that the current sink may be selected before the current source.

Alternatively, after a pair of the current source and current sink have been activated, and current is being transmitted, one of the other sensing components is selected and operated as a respective voltage sensor. Optionally, each one of the other sensing components is sequentially operated and activated as the current voltage sensor.

Figure 13:
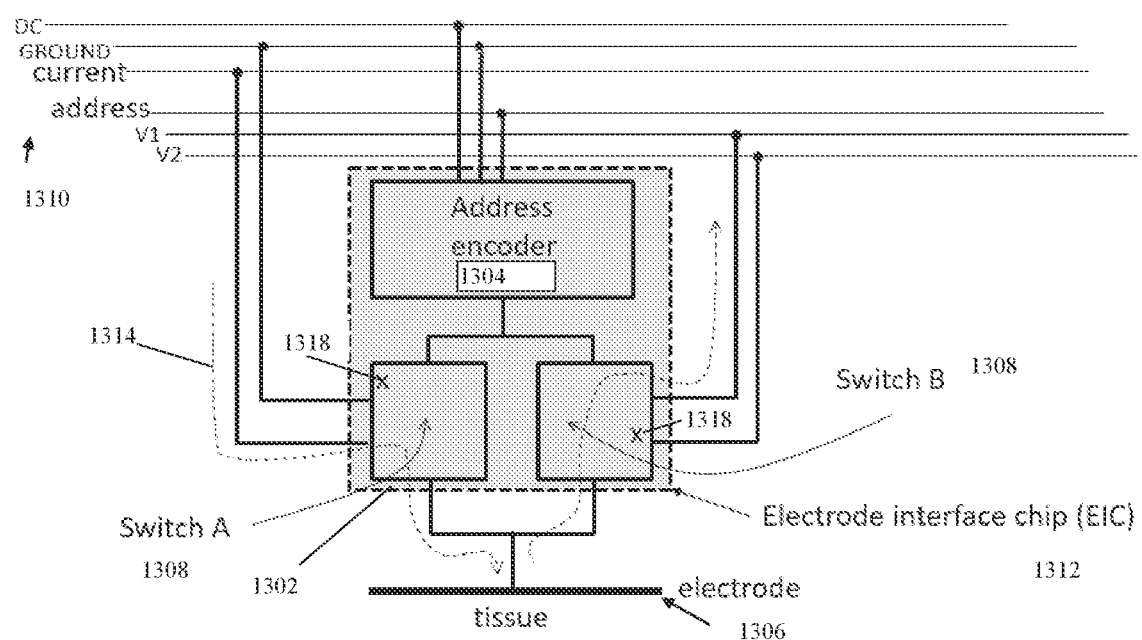
FIG. 13 is a schematic depicting exemplary sub-components of a sensing component, in accordance with some embodiments of the present invention.

Reference is now made to FIG. 13, which is a schematic depicting exemplary sub-components of a sensing component 1302, in accordance with some embodiments of the present invention. Sensing component 1302 includes an address decoder 1304, electrode 1306 for contacting tissue, and one or more switches 1308, as described herein. Sensing component 1302 is connected to a busbar 1310, that includes the following exemplary components, for example, dedicated transmission lines: DC, ground, current, address, V1, and V2, as described herein. Components 1304 and 1308 may be connected to electrode 1306 via an electrode interface chip (EIC) 1312. A current 1314 flows from busbar 1310, to tissue and back via switches 1308 and electrode 1306 in response to activation instructions to operate the sensing component as a current source, and a dedicated address issued by the controller, as described herein.

Figure 14:
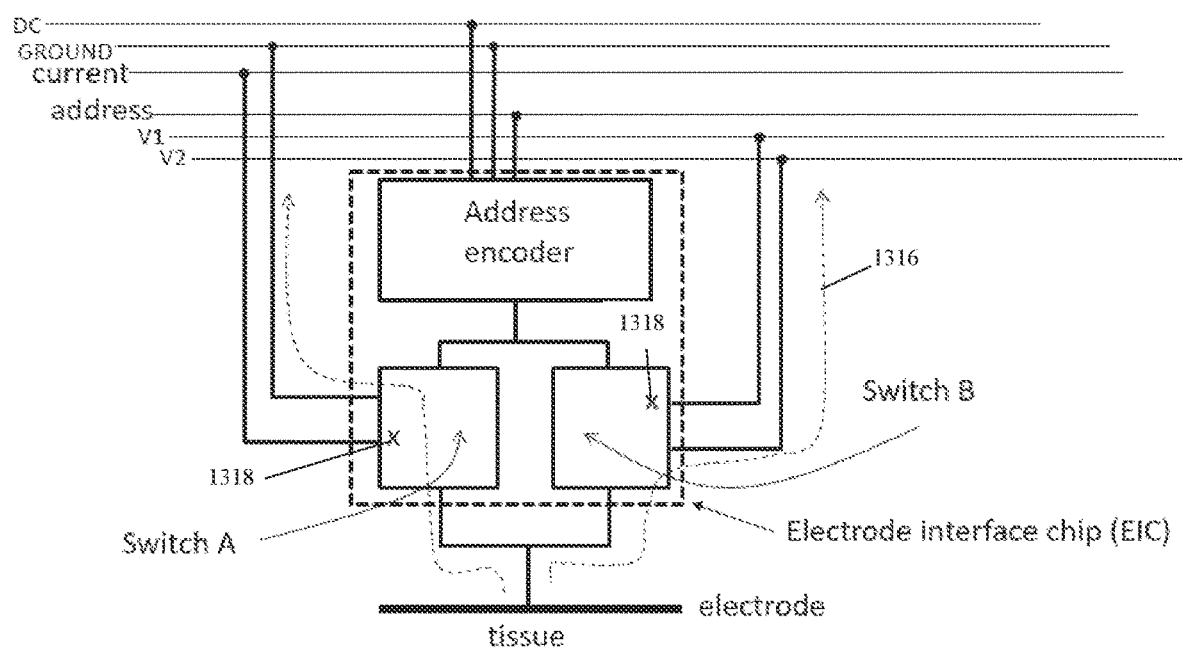
FIG. 14 is a schematic of the sensing component of FIG. 13, depicting current flowing from the tissue to the busbar via the electrode in response to activation instructions to operate the sensing component as a current sink, and a dedicated address issued by the controller, in accordance with some embodiments of the present invention.

Reference is now made to FIG. 14, which is a schematic of the sensing component of FIG. 13, depicting current 1316 flowing from the tissue to the busbar via the electrode in response to activation instructions to operate the sensing component as a current sink, and a dedicated address issued by the controller, in accordance with some embodiments of the present invention.

With reference to FIGS. 13 and 14, the 'x' 1318 depicted inside the switches of the sensing components denote a nonactive channel for distinguishing between sensing components operated as a current injector and another sensing component operated as a current collector.

Referring now back to feature 330 of FIG. 3A, optionally, sensing components are each individually selected and activated and/or operated by instructions generated and transmitted by the controller. Individual control enables random selection of pairs of sensing components for transmission of current. Alternatively, or additionally, sensing components are pre-paired. Pairs are selected and activated and/or operated by instructions generated and transmitted by the controller. A single address and operation mode may represent a pair of sensing components. The pairing enables using a single address and single set of operation instructions to activate and operate the pair of sensing components. Instructions are generated for one sensing component of the pair to connect to a current injection line, and instructions are generated for the other sensing component of the pair to connected to a ground and/or common line. Optionally, two switches are activated per sensing component, optionally a group of four switches at a time (i.e., for a pair of sensing components including a current injection electrode and a current collecting electrode).

Figure 15:
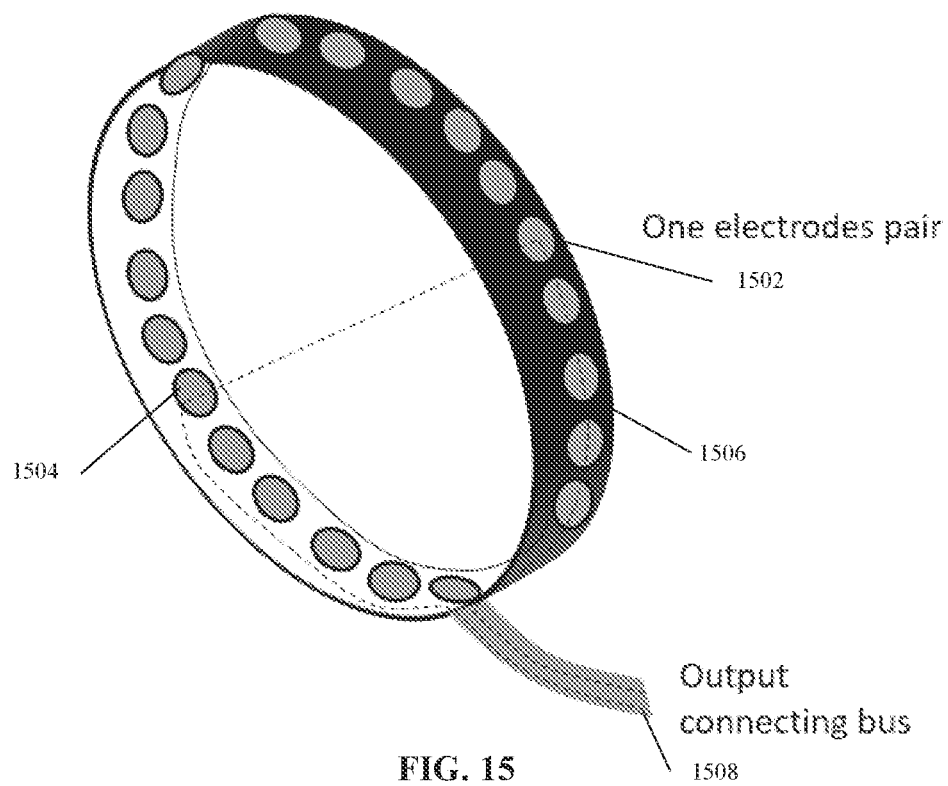
FIG. 15 is a schematic depicting a pair of electrodes of multiple electrodes located on a support element arranged as a circle, which are activated and/or operated as a pair or individually by the controller via a connection busbar, in accordance with some embodiments of the present invention.

Reference is now made to FIG. 15, which is a schematic depicting a pair of electrodes 1502 and 1504 of multiple electrodes located on a support element 1506 arranged as a circle, which are activated and/or operated as a pair or individually by the controller via a connection busbar 1508, in accordance with some embodiments of the present invention.

Figure 16:
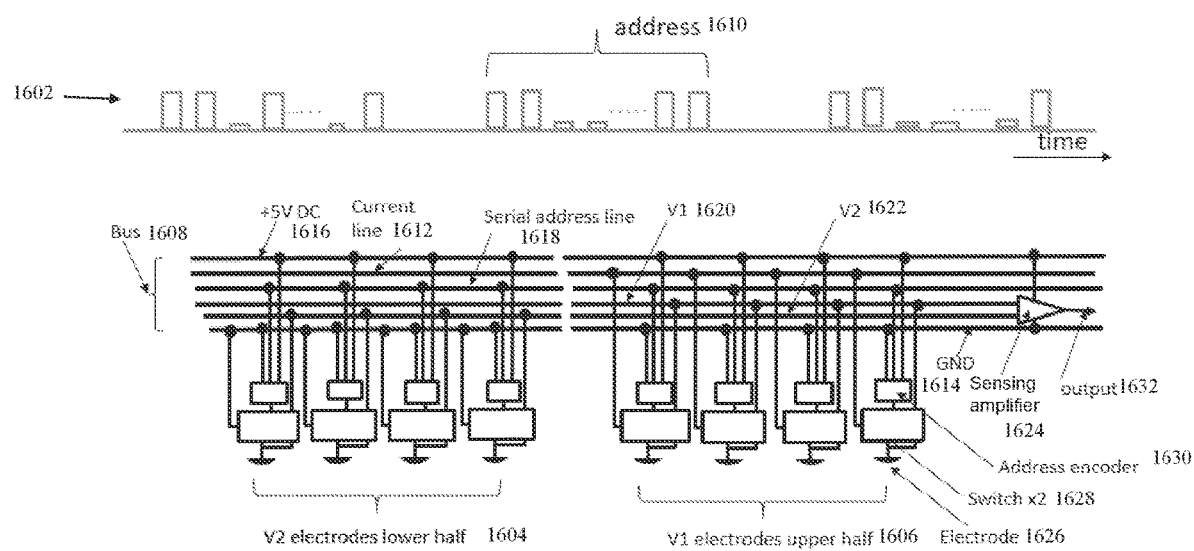
FIG. 16 is a schematic depicting an example of instructions generating for activating and operating a pair of electrodes selected from a bottom set of sensing components and a top set of sensing components using a common busbar, in accordance with some embodiments of the present invention.

Reference is now made to FIG. 16, which is a schematic depicting an example of instructions 1602 generating for activating and operating a pair of electrodes selected from a bottom set of sensing components 1604 and a top set of sensing components 1606 using a common busbar 1608, in accordance with some embodiments of the present invention. Instructions 1602 may be a sequence of bits and/or parallel bits (for a multi-line address busbar component) denoting an address 1610 of the selected electrodes and/or a sequence and/or parallel bits denoting operating mode (e.g., activate switch to connect to current line of the busbar). Electrodes 1604 and 1606 may be arranged in a circle along a support element, as described herein. Instructions may be generated for one sensing component to connect to a current injection line 1612 of busbar 1608, and instructions are generated for the other sensing component to connect to a ground and/or common line 1614 of busbar 1608, forming a pair of electrodes for transmission of current.

Busbar 1608 may include one or more of the following sub-components such as lines: +5V DC line 1616, current line 1612, serial address line 1618, V1 line 1620, V2 line 1622, ground line 1614, Sensing components 1604 1606 may include one or more of the following components: electrode 1626, two switches 1628, address encoder 1630, sensing amplifier 1624, and output 1632 of amplifier 1624.

Referring now back to FIG. 3A, at 340, measurements outputted by the selected sensing component are obtained. The measurements are transmitted over the common busbar (e.g., via a dedicate line component) to the controller. Optionally, only a single sensing component is operated to transmit measurements at a time, to avoid interference over the busbar from other sensing components.

At 350, the controller sequentially activates different sensing components and obtains respective measurements from the activated sensing component, by iterating 330 and 340. The controller may transmit a sequence of the addresses of the selected sensing components. Each sensing component and/or pair thereof may be activated at a respective time according to the transmitted address.

The sensing components are activated according to the measurements used to compute the 3D impedance value dataset for the body portion. In an exemplary implementation, an initialization set of impedance values may be obtained. The initialization set of impedance values may be used for initialization of the parameters of the computational model of the 3D dataset described herein. The initial set of impedance values may be obtained by sequentially activating a respective pair of current source and current sink, and obtaining voltage readings from the respective pair of current source and current sink while current is flowing between the respective pair. Another set of data is obtained, by the controller sequentially activating the current source, current sink, and the voltage sensors. Optionally, for each pair of current source and current sink, the controller sequentially activates each one of the other sensing components as a voltage sensor, for obtaining voltage measurements. The controller then selects another pair of current source and current sink, and controller sequentially activates each one of the other sensing components as a voltage sensor, for obtaining another set of voltage measurements. It is noted that the initialization set may be obtained before the other set of voltage measurements, and/or as part of the process of obtaining the voltage measurements, by obtaining voltage measurements from the sensing components that are operates as the current source and current sink.

Optionally, the controller transmits instructions to terminate operation of the activated sensing component prior to activation of another sensing component. Alternatively, the activated sensing component self terminates, for example, by a timing circuit designed to self terminate the activated sensing component after a predefined amount of time. Alternatively, the sensing components are designed to terminate operation when another sensing component is activated.

The current applied between the selected electrode pair (i.e., of the selected sensing components) may be a direct current and/or an alternating current. The magnitude of the current may be, for example, about or below 150, or 100, or 75 or other micro-ampere p/p values. The frequency of the current may be, for example, in the range of about 100 hertz (Hz) to 100 kiloHz (kHz).

The voltage drop between any two electrodes may be measured.

Impedance values may be computed using Ohm's law in its complex form.

Figure 17:
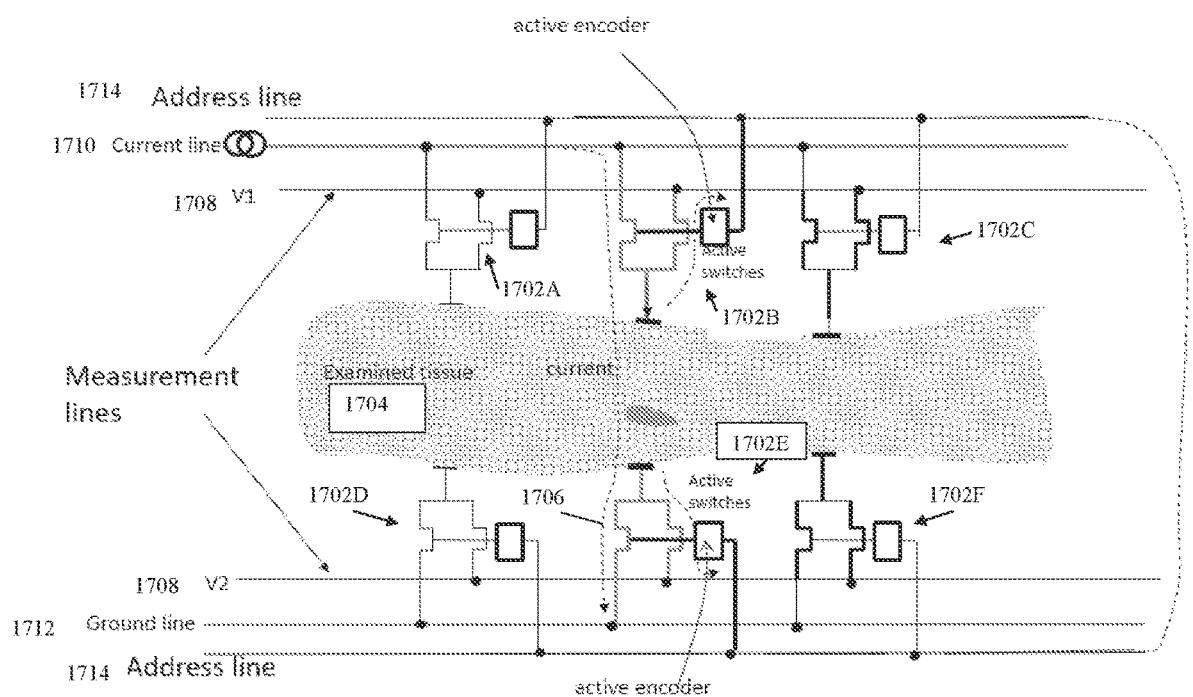
FIG. 17 is a schematic depicting sequential activation of sensing components for obtaining measurements for generation of a 3D impedance dataset of an examined tissue, in accordance with some embodiments of the present invention.

Reference is now made to FIG. 17, which is a schematic depicting sequential activation of sensing components 1702A-F for obtaining measurements for generation of a 3D impedance dataset of an examined tissue 1704, in accordance with some embodiments of the present invention. Sensing components 1702B and 1702E are sequentially activated to act as respective current source and current sink for transmission of a current 1706 through examined tissue 1704 (via current line 1710 and ground line 1712 of the busbar), as described herein. Other sensing components 1702A, 1702C, 1702D, and 1702F are sequentially activated as voltage sensors for obtaining voltage measurements (via measurement lines 1708 of the busbar) while current 1706 is being transmitted, as described herein. Sequential activation is via respective unique addresses transmitted on address line 1714 of the common busbar, as described herein.

At 360, the obtained sets of measured currents and voltages and/or impedance values, optionally for each pair of current source and current sink, are provided for further computation and/or analysis. The obtained measurements may be locally stored, and/or transmitted over the network to a remote server for remote processing. The remote processing may reduce computation time for generating the 3D dataset, such as when the computational hardware of the remote server is much more powerful than the locally available computational capabilities.

Collecting the measurement (e.g., for computing resistance and/or impedance) may enable, for example, using mathematical manipulation similar to the inverse Radon transformation, to create the desired 3D impedance image and/or map of the imaged tissue, as described herein.

At 370, a 3D dataset of impedance values of the body portion is computed from the measured current, voltage, and/or impedance values. The 3D dataset may be based on an initialization dataset where impedances are computed based on current iteratively applied between two active electrodes (i.e., of the sensing components), with other non-selected electrodes not being utilized. Alternatively, or additionally, the 3D dataset is computed based on the two active electrodes transmitting current therebetween and the other (e.g., each one of the other) electrodes acting as voltage sensors, where the initialization dataset ma serve as initial values for computation of the 3D dataset, as described herein.

Optionally, the 3D dataset is divided into individual 3D cells. A respective impedance value is computed for each of the 3D cells. The size of each cell may be defined, for example, by the spacing of the sensing components, and/or by the resolution obtained by the sensing components. Alternatively, the 3D dataset is defined as continuous values, for example, by functions that map coordinates in the 3D space to impedance values.

Figure 18:
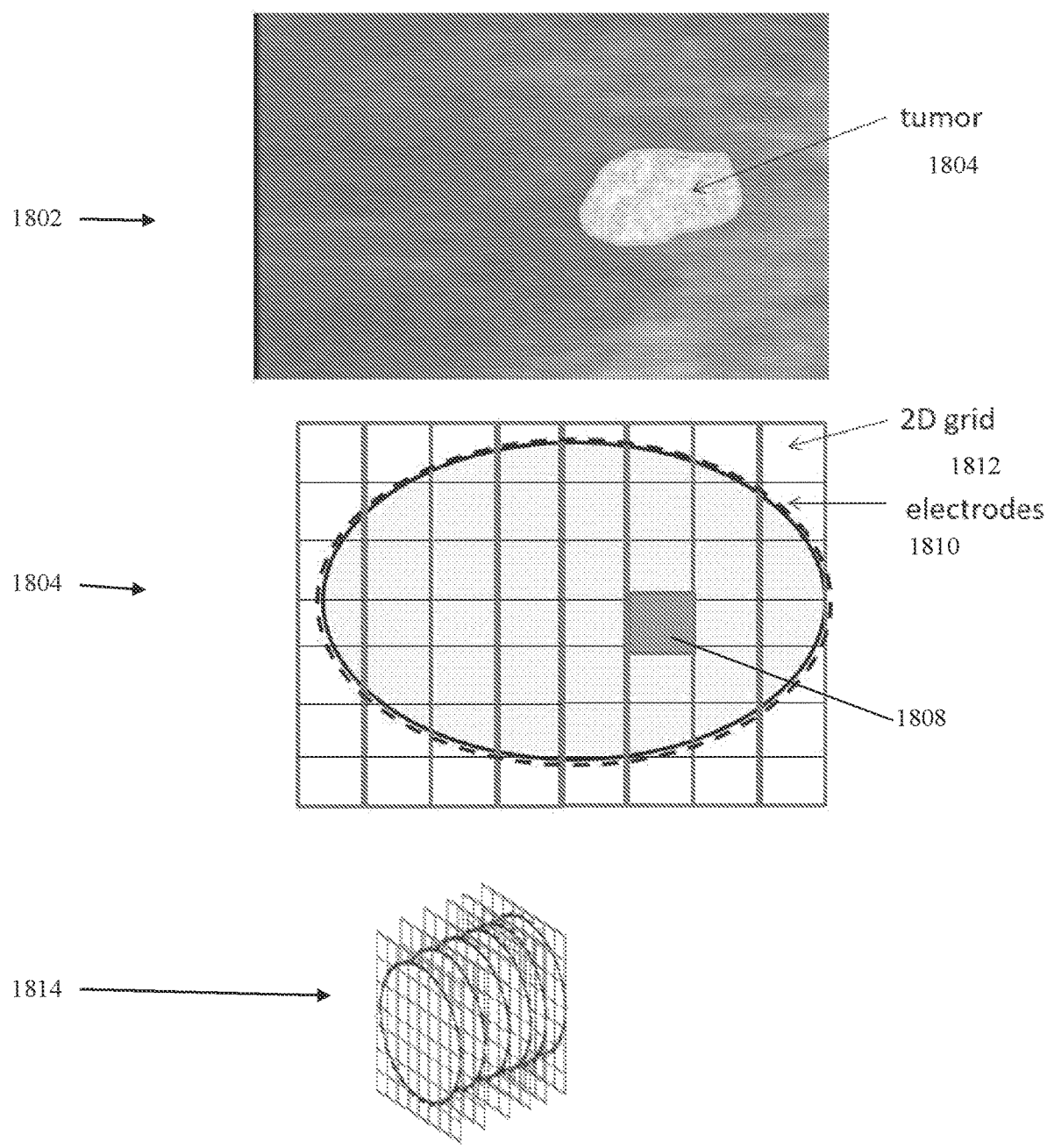
FIG. 18 includes schematics to help understand the 3D dataset, in accordance with some embodiments of the present invention.

Reference is now made to FIG. 18, which are schematics to help understand the 3D dataset, in accordance with some embodiments of the present invention. Schematic 1802 is an exemplary image obtained from a standard mammogram machine, that depicts a tumor 1804. Schematic 1806 depicts a 2D grid of cells 1812, where tumor 1808 is shown for a cell as a whole. Sensing components 1810 (e.g., electrodes thereof) are depicted around the perimeter of the tissue. Schematic 1814 depicts a 3D dataset, created as described herein (and/or slice by slice).

Referring now back to FIG. 3A, at 370, Optionally, the 3D dataset is computed based on the following exemplary implementation. First, a summary is provided, followed by a detailed mathematical description. Values for the 3D dataset are obtained by a computational model of the 3D impedance values of the body portion. The 3D dataset may first be initialized using the initialization set of impedance values (obtained as described herein), which may be based on the assumption that current travels in a straight line between the current source and current of the different pairs of sensing components. The initialization dataset includes conductivity distribution values. Now, the measured voltages and currents obtained for each pair of current source and current sink are compared to computed boundary values obtained from the computational model, which includes Laplace's equation incorporating the distributed conductivity (initialized using the initialization dataset, and then adjusted as described herein). The comparison is based on the observation that internal values within the body portion cannot be directly measured (since not sensor is placed within the tissue) but are computed, while values on the surface of the body portion are measured by the sensing components. The computational model is adjusted until the obtained voltages and currents match the computed boundary values within an error range.

It is noted that in some implementations, the initialization dataset may be sufficiently accurate, and the full 3D dataset is not necessarily required.

The initialization dataset may be computed as a line integral, or in a discreet case as a sum of incremental resistances between pairs of active electrodes (i.e., of each currently operated sensing component).

Optionally, the initialization dataset is computed by collecting of measurements (e.g., resistances, impedance, voltage, current) slice by slice. The single slice model may be considered as an array and/or grid of cells denoting resistors or more general form an impedance containing a real and/or an imaginary component. Alternatively, or additionally, the initialization dataset is computed volume wise, by selecting electrode pairs where imaginary straight lines between the selected pairs are non-parallel.

Optionally, the number of measurements performed by activated pairs of sensing components may be larger than the number of the data components used to calculate the impedance value.

As used herein, the terms "impedance" and "resistance" may sometimes be interchanged.

Figure 19:
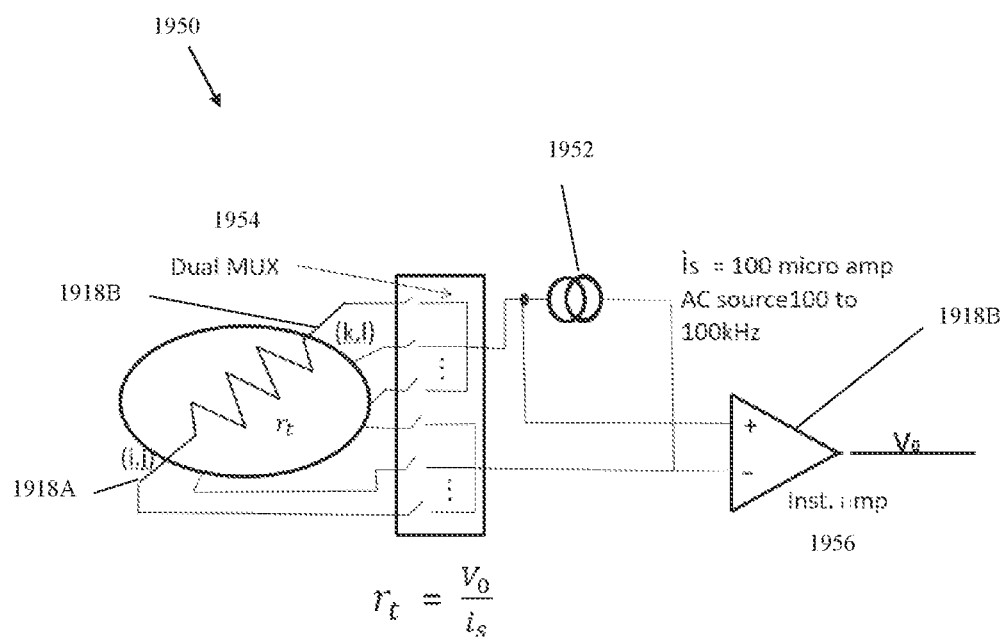
FIG. 19 is a schematic of a measurement setup depicting one example of an impedance measurement, in accordance with some embodiments of the present invention.

Reference is now made to FIG. 19, which is a schematic of a measurement setup 1950 depicting one example of an impedance measurement, from a first selected individually addressable electrode 1918A denoted (i,j) to a second selected individually addressable electrode 1918B denoted (k,l) (or where the pair of electrodes is selected by an individual address), in accordance with some embodiments of the present invention. Measurement setup 1950 includes an AC constant current source 1952, may include a dual MUX 1954, and an instrumentation amplifier 1956. The sum of the partial, digitized impedances between electrodes 1918A and 1918B is measured. In terms of mathematical representation, the value $R_{i,j,k,l}$ is computed.

Impedance measurements may be performed slice wise, for example, to collect parallel slices (e.g., 2D) which are arranged into a 3D volumetric image. The support elements and corresponding electrodes may be arranged to collect slice data, for example, each support element is arranged as a partial (or complete) ring for collecting slice data of the tissue encapsulated within the ring, as described herein, for example, with reference to FIG. 15. In such a case, the second index may be the same for all electrodes belonging to the same slice, mathematically denoted by $R_{i,j}$.

Alternatively or additionally, impedance measurements may be performed non-parallel to collect data for computing the 3D volumetric image, such as in a cross-slice manner. The values k,l may belong to a different slice in the case of cross slice measurements.

Figure 20:
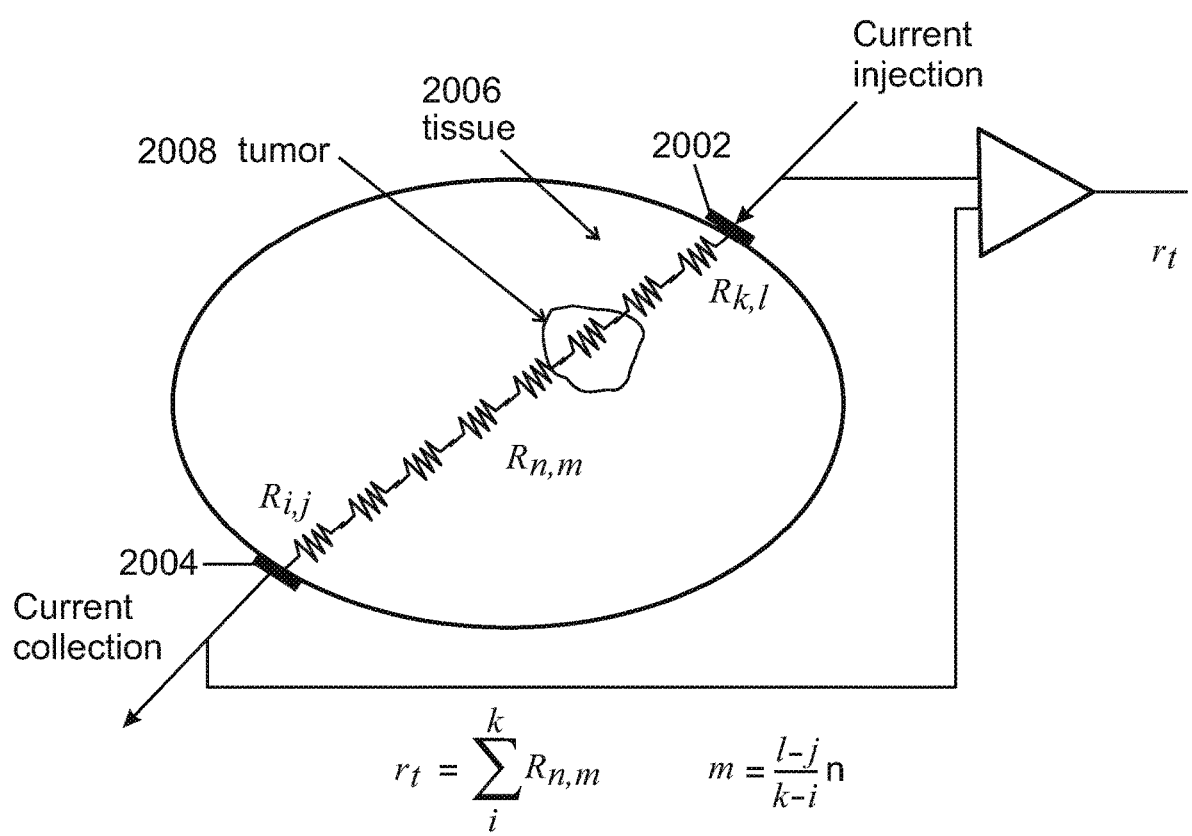
FIG. 20 is a schematic depicting a single measurement of path resistance (and/or impedance) for computation of a 3D dataset, in accordance with some embodiments of the present invention.

Reference is now made to FIG. 20, which is a schematic depicting a single measurement of path resistance (and/or impedance) for computation of a 3D dataset, in accordance with some embodiments of the present invention. Selected pair of electrodes (of sensing components) 2002 and 2004 transmit current therebetween. The current is transmitted through a tissue 2006 which includes a tumor 2008. The overall resistance between E02 and E04 is denoted $r_t$, which may be computed using the following equation, which denotes the sum of all discretized impedances between the electrodes, forming a linear equation with the impedances as unknowns.

$$r_t = \sum_i^k R_{n,m}$$

Figure 21:
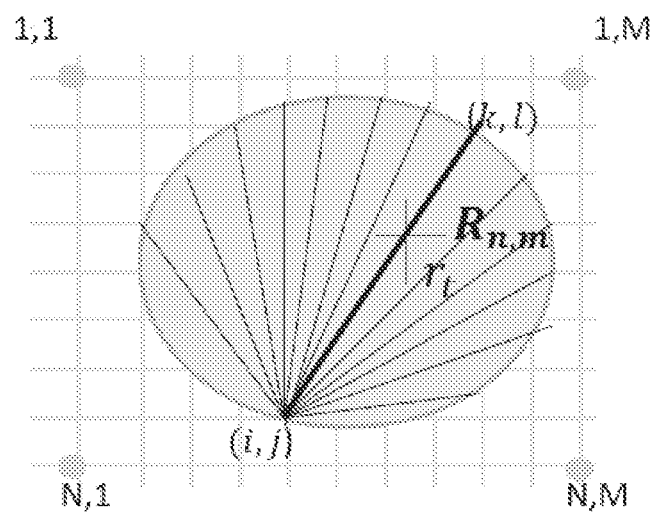
FIG. 21 is a schematic depicting the computation of impedance values as described with reference to FIG. 20 repeated sequentially for each pair of electrodes, in accordance with some embodiments of the present invention.

Reference is now made to FIG. 21, which is a schematic depicting the computation of impedance values as described with reference to FIG. 20 repeated sequentially for each pair of electrodes, in accordance with some embodiments of the present invention.

Reference is now made to FIG. 22, which depicts a matrix representation of vectors of impedance measurements obtained as described with reference to FIG. 21, in accordance with some embodiments of the present invention.

The matrix representation may be mathematically denoted as:

$$r = AR$$

Where:

r denotes the measurement vector, i.e., the impedances as computed from measured currents and/or voltages, R denotes the vector of the unknown impedances, A denotes a weight matrix of binary elements.

The vector R which forms the tissue tomography may be computed by generating the inverse (e.g., generalized inverse since dim(r)) of matrix A, denoted $A^{-1}$, yielding the following equation:

$$R = A^{-1} r$$

Arranging the elements of R enables generation of a tomographic impedance map (i.e., the 3D dataset) as described herein.

Reference is now made to FIG. 23, which is a schematic depicting a solution vector denoted R (e.g., as in FIG. 22) rearranged as an impedance matrix representing a 3D dataset, in accordance with some embodiments of the present invention. The impedance matrix may be 2D and/or 3D. The impedance matrix may be presented as an image, for exampling, assigning pixel intensity values (e.g., color, grey) corresponding to the values of the cells of the impedance matrix, as described herein. Malignancies may be detected by cells of the impedance matrix having values that are significantly different than other background and/or neighboring cells, for example, pixels having color and/or grey shading that is different than the color and/or shading of the rest of the tis sue.

The obtained 3D dataset may be used as the initialization set of conductivity distribution values of the computational model of the 3D dataset. Further adjustment of the computational model to increase accuracy of the computed conductivity distribution is described below. Alternatively, the method directly continues to feature 380, where the 3D dataset of conductivity distribution values may be analyzed directly (without adjustment of the computational model), for example, to detect malignancy and/or anomalies, as described herein.

Optionally, the impedance measurements are processed and/or analyzed, to reduce or prevent errors. When observing the current propagation in tissue the simplistic assumption of current traveling between electrodes in a straight line trajectory may lead to false impedance mapping. The false impedance mapping effect poses a technical problem in obtaining high accuracy and/or high resolution impedance images.

Figure 24:
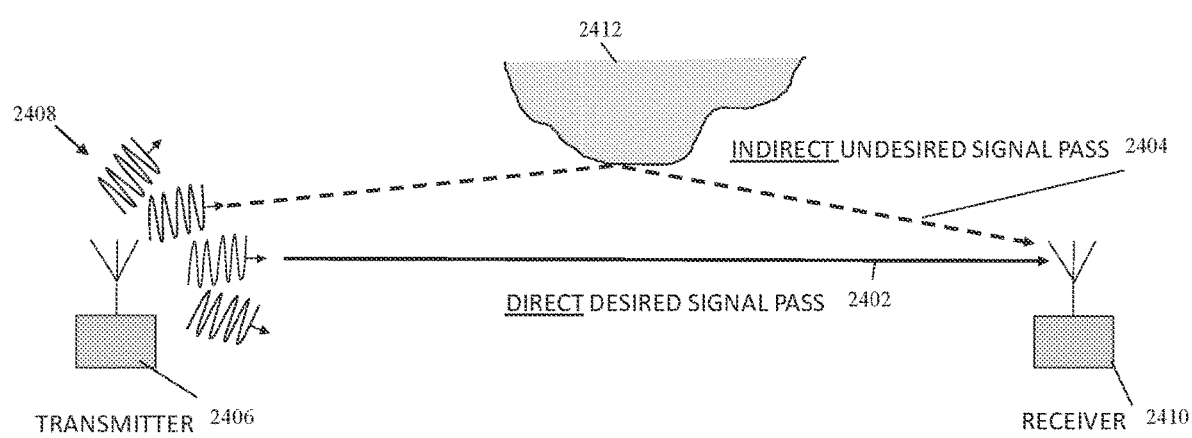
FIG. 24 is a schematic that depicts in a high level the technical problem in which a direct desired signal is interfered with an indirect undesired signal, to help understand some embodiments of the present invention.

Reference is now made to FIG. 24, which is a schematic that depicts in a high level the technical problem in which a direct desired signal 2402 is interfered with an indirect undesired signal 2404 (also referred to as a multi pass signal), to help understand some embodiments of the present invention. A transmitter 2406 (e.g., television broadcaster) transmits signals 2408 for reception by a receiver 2410 (e.g., television). An object (e.g., mountain) 2412 reflects signals 2408, resulting in indirect undesired signal 2404, which interferes at receiver 2410 with direct desired signal 2402, for example, creating ghost images on the television display. It is noted that direct desired signal 2402 arrives at receiver 2410 before indirect undesired signal 2404. As such, in at least some implementations of the systems, methods, apparatus, and/or code instructions described herein, gating may be used to select the first arriving impedance measurement at the receiving electrode in order to prevent or reduce interference effects.

Figure 25:
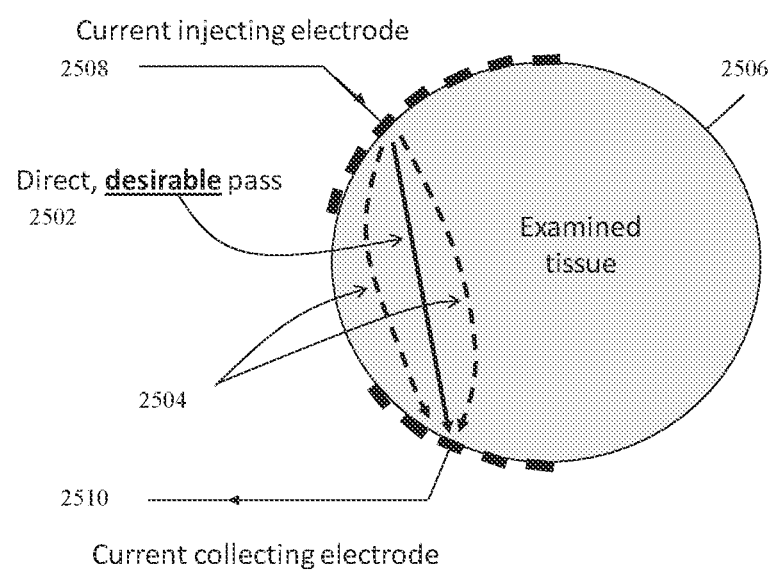
FIG. 25 is a schematic that depicts the technical problem in which a direct desired signal is interfered with an indirect undesired signal in the implementation of generating impedance based images for a target tissue, to help understand some embodiments of the present invention.

Reference is now made to FIG. 25, which is a schematic that depicts the technical problem in which a direct desired signal 2502 is interfered with an indirect undesired signal 2504 in the implementation of generating impedance based images for a target tissue 2506, to help understand some embodiments of the present invention. A current injecting electrode 2508 injects current into tissue 2506 for collection by a current collecting electrode 2510. The injected current includes direct desired signal 2502 which travels directly between electrodes 2508 and 2510, and undesired signal 2504 which does not travel directly between electrodes 2508 and 2510. In at least some implementations of the systems, methods, apparatus, and/or code instructions described herein, undesired signal 2504 is eliminated or reduced by gating which allows only for the first arriving direct desired signal 2502 to be selected. Alternatively, direct desired signal 2502 is obtained by solving the corresponding Laplace equations as described herein. Due to the multiple current trajectories 2502 and X04, the ray type tomography may be modified, as described herein.

The following is an exemplary process for overcome and/or reducing the effects of the false mapping effect, which may provide more accurate impedance measurement and/or for increasing accuracy of the initial dataset of conductivity mapping and/or impedance values. For clarity of explanation, the process is first described with reference to the 2D Cartesian plane (i.e., x,y coordinate) case (e.g., in the implementation where 2D slices are computed and arranged into the 3D image), which is expanded into the 3D case (e.g., in the implementation where the 3D image is computed from the impedance measurements without the intermediate 2D slice computation). It is noted that alternatively to the process described below, gating may be used to select the first arriving current signal, and excluding and/or ignoring subsequently arriving signals.

The exemplary process is based on an iterative approximation of conductivity (and/or inverse resistivity) denoted $\sigma(x,y)$, by repeated solution of the following corresponding Laplace equation:

$$\nabla \cdot \sigma(x,y) \nabla u(x,y) = 0$$

Where: u(x,y) denotes the potential at 2D coordinates denoted (x,y), with proper boundary conditions, and the use of a Jacobian type matrix as described herein. $\sigma(x,y)$ denotes the mapping indicating the location of the region of interest (e.g., tumor, malignancy, abnormality, suspicious clinical finding).

The following is a mathematical process for finite different approach for the 2D implementation for solving for the mapping denoting region of interest in the intra-body image:

$$\nabla \cdot \sigma \nabla u = 0$$

$$\frac{\partial}{\partial x}\left(\sigma \frac{\partial u}{\partial x}\right) + \frac{\partial}{\partial y}\left(\sigma \frac{\partial u}{\partial y}\right) = 0$$

Hence:

$$\frac{\partial \sigma}{\partial x}\frac{\partial u}{\partial x} + \sigma \cdot \frac{\partial^2 u}{\partial x^2} + \frac{\partial \sigma}{\partial y}\frac{\partial u}{\partial y} + \sigma \cdot \frac{\partial^2 u}{\partial y^2} = 0$$

Figure 26:
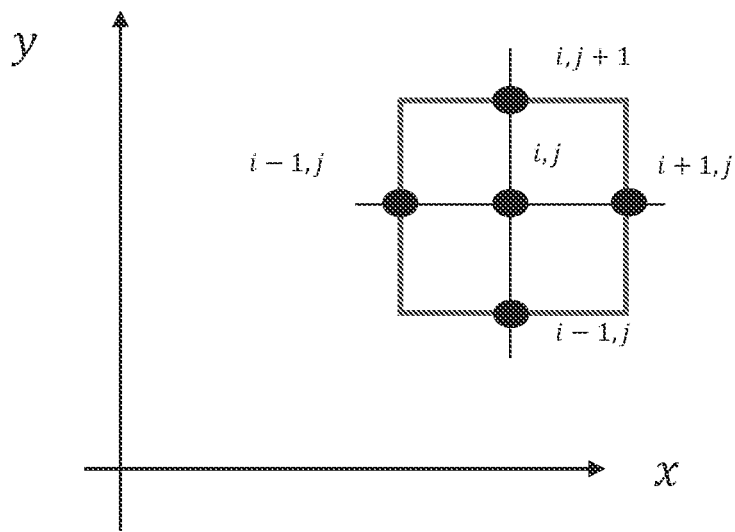
FIG. 26 is a schematic of a finite difference numerical solution 2D grid for helping to understand the mathematical process for finite difference approach for solving for the region of interest of the intra-body image, in accordance with some embodiments of the present invention.

Reference is now made to FIG. 26, which is a schematic of a finite difference numerical solution 2D grid for helping to understand the mathematical process for finite difference approach for solving for the region of interest of the intra-body image, in accordance with some embodiments of the present invention.

$$\frac{\partial u}{\partial x} \approx 0.5(u_{i+1,j} - u_{i-1,j}) \quad \frac{\partial u}{\partial y} \approx 0.5(u_{i,j+1} - u_{,j-1})$$

$$\frac{\partial \sigma}{\partial x} \approx 0.5 \cdot (\sigma_{i+1,j} - \sigma_{i-1,j}) \quad \frac{\partial \sigma}{\partial y} \approx 0.5 \cdot (\sigma_{i,j+1} - \sigma_{i,j-1})$$

$$\frac{\partial^2 u}{\partial^2 x} \approx u_{i+1,j} - 2u_{i,j} + u_{i-1,j} \quad \frac{\partial^2 u}{\partial^2 y} \approx u_{i,j+1} - 2u_{i,j} + u_{i,j-1}$$

$$\frac{\partial \sigma}{\partial x}\frac{\partial u}{\partial x} + \sigma \cdot \frac{\partial^2 u}{\partial x^2} + \frac{\partial \sigma}{\partial y}\frac{\partial u}{\partial y} + \sigma \cdot \frac{\partial^2 u}{\partial y^2} = 0$$

⇩

$$0.25[(\sigma_{i+1,j} - \sigma_{i-1,j}) \cdot (u_{i+1,j} - u_{i-1,j}) + (\sigma_{i,j+1} - \sigma_{i,j-1}) \cdot (u_{i,j+1} - u_{,j-1})] +$$
$$\sigma_{i,j} \cdot [u_{i+1,j} + u_{i-1,j} + u_{i,j+1} + u_{i,j-1} - 4 \cdot u_{i,j}] = 0$$

The above equation yields the solution of the potential field denote:

$$u_{i,j}$$

The obtained values for the boundary potential are compared with the measured values and the deviation is corrected by perturbing the values of the conductance field denoted $$\sigma_{i,j}$$

The above process described for the 2D implementation is now described for the 3D implementation.

Figure 27:
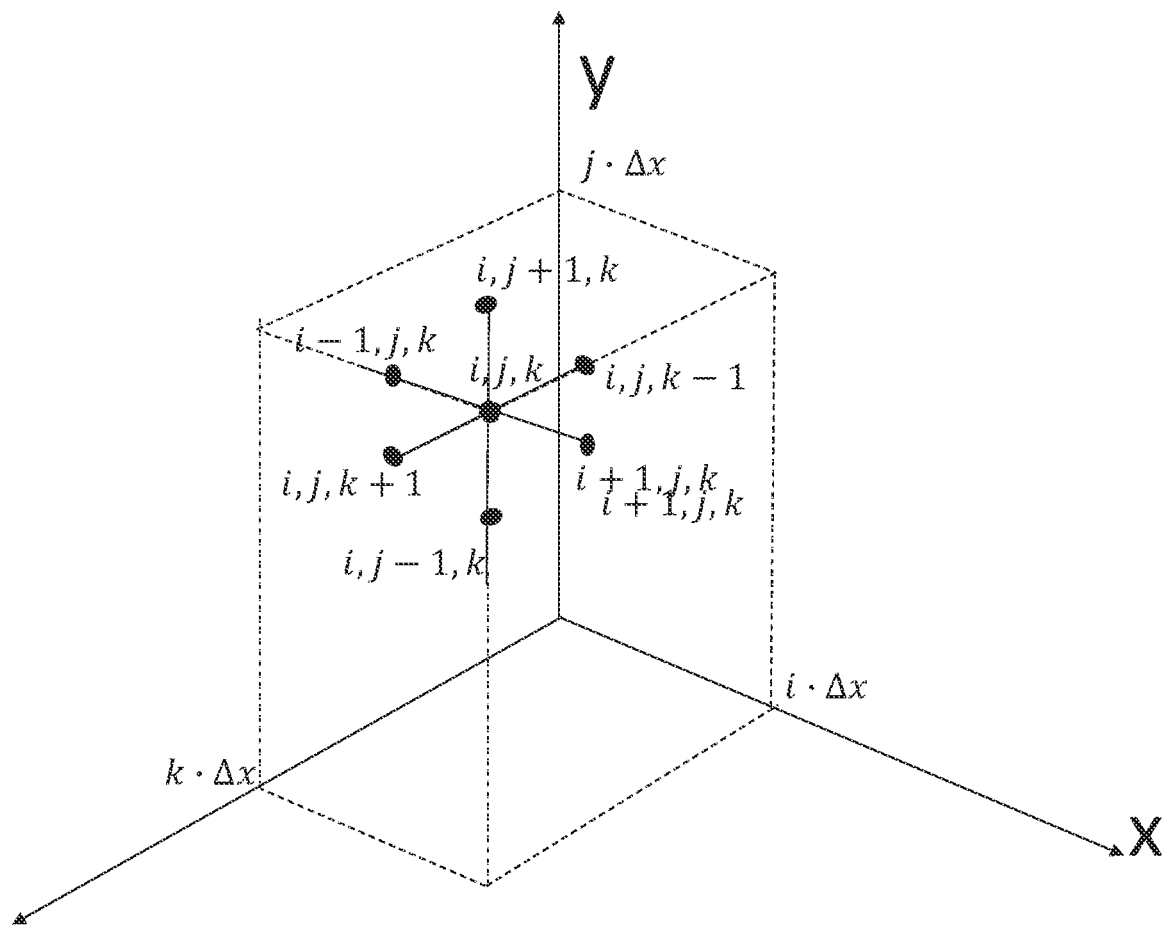
FIG. 27 is a schematic of a 3D coordinate system for helping to understand the exemplary mathematical process for solving for the region of interest of the intra-body image, in accordance with some embodiments of the present invention.

Reference is now made to FIG. 27, which is a schematic of a 3D coordinate system for helping to understand the exemplary mathematical process for solving for the region of interest of the intra-body image, in accordance with some embodiments of the present invention.

Assuming an initial value for conductivity denoted $\sigma_0 = \sigma_{i,j,k}$ ∀i,j,k stat calculating ∀i,j:

$$0.16667[(\sigma_{i+1,j,k} - \sigma_{i-1,j,k}) \cdot (u_{i+1,j,k} - u_{i-1,j,k}) + (\sigma_{i,j+1,k} - \sigma_{i,j-1,k}) \cdot (u_{i,j+1,k} - u_{i,j-1,k}) + (\sigma_{i,j,k+1} - \sigma_{i,k-1}) \cdot (u_{i,j,k+1} - u_{i,k-1})] + \sigma_{i,j,k}[u_{i+1,j,k} + u_{i-1,j,k} + u_{i,j+1,k} + u_{i,j-1,k} + u_{i,j,k+1} + u_{i,k-1} - 6 \cdot u_{i,j,k}] = 0$$

Solving for $u_{i,j,k}$ for all i=1 . . . N, j=1 . . . M, k=1 . . . K. It is noted that the resulting boundary values will naturally differ from the measured boundary condition:
Defining the measured boundary values as a vector denoted: $v_s^m$ for s=1 . . . S
And the calculated boundary conditions denoted as:

$$v_s^c \text{ for s=1 ... S}$$

Defining the error norm denoted as:

$$E = \|v_s^m - v_s^c\|$$

For the initial value guessed for σ, making a small change Δσ of $\sigma_{i,j,k}$ to $\sigma_{i,j,k} + \Delta\sigma$ and calculating the resulting change in the boundary values.
When the change resulted an increase in the deviation denoted:

$$E_{new} > E_{old}$$

Inversing the change and set the following mathematical representation:

$$\Delta\sigma = -\Delta\sigma$$

Repeating the calculations for all i's, j's and k's yields the Jacobi type sensitivity tensor denoted as:

$$J = \frac{\Delta v_s^c}{\Delta \sigma_{i,j,k}}$$

Resolving the Laplace equation with new values for the conductance distribution denoted as:

$$\sigma_{i,j,k}(\text{new}) = \sigma_{old} + \Delta\sigma_{i,j,k}$$

where $\Delta\sigma_{i,j,k}$ is calculated as described sequentially, where each of the Δ's reduces the error functional denoted E. When the error functional gets lower than a predefined limit denoted Emin, the process may be halted and the latest mapping of the conductivity denoted $\sigma_{i,j,k}$ is displayed, for example, depicting the region of interest.

Figure 28:
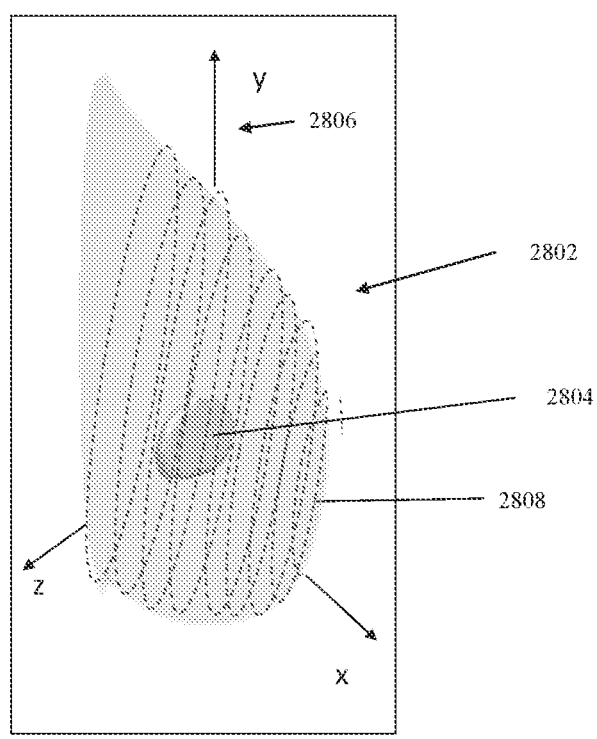
FIG. 28 is a schematic depicting a 3D resistance and/or conductance mapping of a breast denoting an identified tumor therein, in accordance with some embodiments of the present invention.

Reference is now made to FIG. 28, which is a schematic depicting a 3D resistance and/or conductance mapping 2802 of a breast denoting an identified tumor 2804 therein, in accordance with some embodiments of the present invention. The 3D mapping 2802 and tumor 2804 are computed according to the exemplary 3D mathematical process described herein. The 3D mapping 2802 and tumor 2804 are depicted with respect to an exemplary 3D coordinate system, as described herein. Example boundaries used in the mathematical process are denoted by dotted lines 2808.

Figure 29:
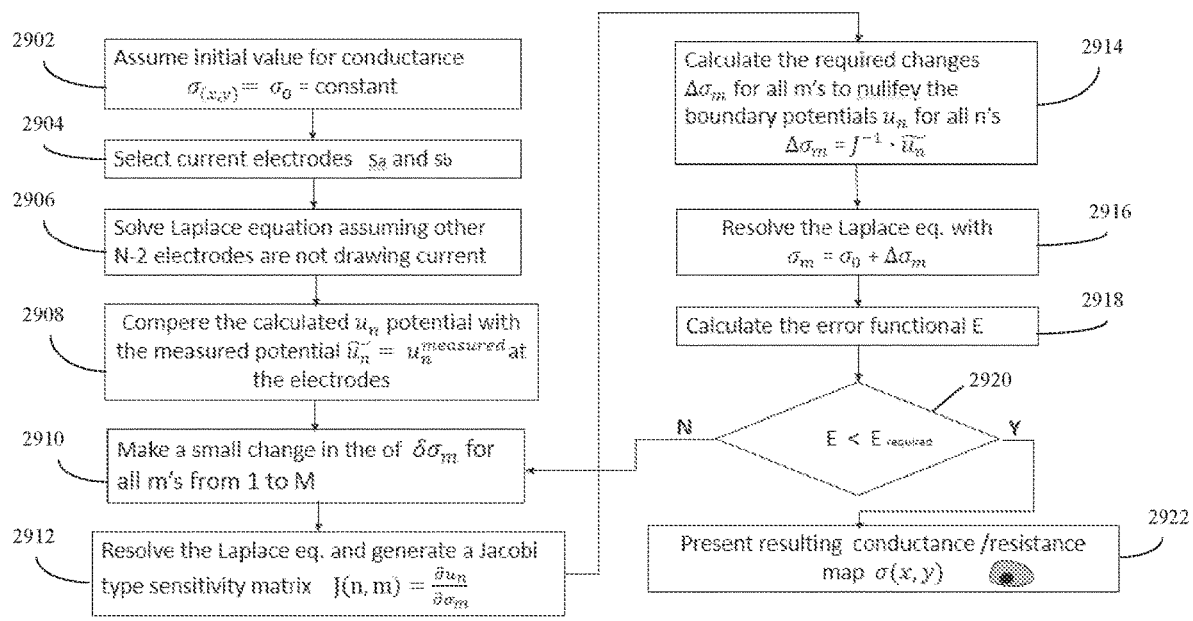
FIG. 29 is a flowchart of an exemplary mathematical process for computing a conductance and/or resistance field including a region of interest denoting an intra-body image, for example, a tumor in a breast, in accordance with some embodiments of the present invention.

Reference is now made to FIG. 29, which is a flowchart of an exemplary mathematical process for computing a conductance and/or resistance field including a region of interest denoting an intra-body image, for example, a tumor in a breast, in accordance with some embodiments of the present invention. Additional details of the exemplary process are as described herein.

At 2902, an initial value for conductance distribution mapping (sometimes referred to herein as the initial dataset) denoted $\sigma_{(x,y)} = \sigma_0 =$ constant is selected. Alternatively, the initial value of the conductance distribution mapping is obtained as described herein with reference to the initial dataset, for example, by iteratively activating different pairs of sensing components and measuring impedance.

At 2904, electrodes denoted $S_a$ and $S_b$ are selected for impedance mapping, optionally using an associated addressed, accessed by a conductor coupled to multiple other electrodes, as described herein.

At 2906, the Laplace equation is solved, assuming the other electrodes are not drawing current.

At 2908, the calculated potential denoted $u_n$ is compared with the measured potential at the electrodes, denoted $\tilde{u}_n = u_n^{measured}$. Voltages are measured at the other sensing components not currently selected for transmission of current, by the controller sequentially activating and instructing the other sensing components to operate as voltage sensors, as described herein.

At 2910, a small change is denoted $\delta\sigma_m$ is made for all m's, denoted 1 to M. The amount of small change may be selected, for example, manually defined by a user, based on a predefined system configuration parameter stored in memory, and/or computed by code.

At 2912, the Laplace equation is resolved. A Jacobi type sensitivity matrix denoted $$J(n, m) = \frac{\partial u_n}{\partial \sigma_m}$$

is generated.

At 2914, the changes denoted $\Delta\sigma_m$ for all m's to nullify the boundary potentials denoted $u_n$ for all n's is computed, where $\Delta\sigma_m = J^{-1} \cdot \tilde{u}_n$.

At 2916, the Laplace equation is resolved with $\sigma_m = \sigma_0 + \Delta\sigma_m$.

At 2918, the error function denoted E is calculated. The amount of error that is tolerated may be selected, for example, manually defined by a user, based on a predefined system configuration parameter stored in memory, and/or computed by code.

At 2920, when the value of the error function is below a threshold, the process proceeds to 2922. Alternatively, when the value of the error function is not below the threshold, the process proceeds back to 2910.

At 2922, the resulting distributed conductance and/or resistance map (denoted σ(x,y) for the 2D implementation) is provided (e.g., presented on a display). The map may denote the region of interest (e.g., tumor, malignancy, suspicious tissue), as described herein. The process described herein may be adapted to provide a 3D map, as described herein.

The generation of the 3D distributed conductivity dataset, based on the iterative mathematical process described herein may be computationally intensive, in particular when a large number of sensing components are used, generating a large number of voltage, current, and/or impedance measurements. The computation may be performed by a server that includes sufficient computational resources (e.g., memory, processors) to compute the 3D distributed conductivity dataset within a reasonable amount of time. The voltage, current, and/or impedance measurement may be locally collected, transmitted over a network to the remote server for computation of the 3D map, and the generated 3D dataset may be transmitted to a client terminal over the network for presentation and/or analysis, as described herein.

At 380, the 3D dataset of impedance values and/or the 3D conductivity distribution mapping is analyzed, and/or an impedance based intra-body 3D image of the body portion is generated from the 3D dataset. The analysis may be performed using the generated 3D image. The 3D image may be referred to as a reconstructed image.

Optionally, the analysis of the body portion is for tissue anomaly observation.

Optionally, the analysis of the body portion is for planning treatment of the patient.

Optionally, the analysis includes detection of indication of likelihood of malignancy in the body portion, and/or detection of other clinical abnormality detectable by impedance mapping such as bleeding (e.g., in the brain). Alternatively or additionally, the analysis includes localization of the likelihood of malignancy (and/or other clinical abnormality) in the body portion. The localization and/or detection may be performed, for example, by segmenting tissue indicative of likelihood of malignancy depicted in the 3D image and/or the 3D dataset. The detection and/or segmentation may be performed, for example, by a machine learning model (e.g., neural network) trained on a training dataset of a multiple 3D impedance images and/or 3D datasets with labeled malignancy and/or abnormalities (e.g., delineated in the 3D dataset, and/or external global label) obtained from multiple sample patients. The machine learning model may be iteratively updated with new sample data obtained during user. The iterative improvements may improve quality (e.g., accuracy) of the diagnosis. The machine learning model may be trained and/or updated using sample data from patients in different hospitals, and/or clinics, which may create a diverse training set of patients of for example, different nationalities, ethnicities, demographic backgrounds, economic background, and/or medical background. In contrast to learning on a limited number of patients (e.g., per site) which may not necessarily display sufficient diversity, the diversity of patient data may increase accuracy of detection. The machine learning model may be remotely located in a computing cloud for processing data received from different patients and/or at different sites, and/or for being trained using data from different patients and/or at different sites.

The 3D image and/or analysis results may be presented on a display, stored in a memory (e.g., in the patient's electronic health record), and/or forwarded to another process (e.g., stored locally and/or on a remote device) for additional processing.

The 3D tissue may be presented and/or analyzed as a set of 2D layered images (e.g., 2D slices). Each 2D slice may be separately examined for tumors, for example, manually and/or automatically. The collection of the 3D images may be rendered to form a 3D reconstruction. The resulting 3D reconstruction may be viewed as a whole or the 3D dataset may be sliced (e.g., by a user) at any plane to view the internal details. When automatic tumor segmentation is applied, the findings inside the 3D image may be colored and/or marked by a fill pattern on the display to assist the observer.

The 3D dataset may be computed based on finite element analysis methods. The volume denoting the target body portion may be divided into regions (e.g., triangle shaped) for generating the 3D dataset using the finite element process. The initialization dataset may be used to provide initial values for computation of the impedance values assigned to internal regions using the finite element analysis processes.

Figure 30:
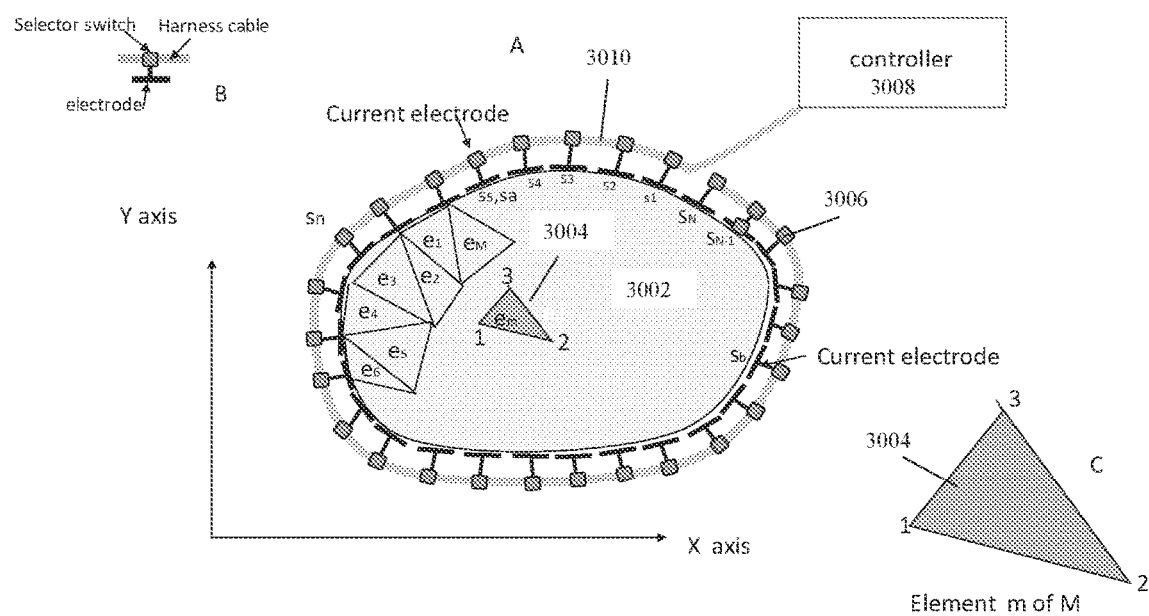
FIG. 30 is a schematic depicting an example of division of an internal tissue of a patient into regions for finite element analysis using data obtained by sensing components located on the boundary of tissue, in accordance with some embodiments of the present invention.

Reference is now made to FIG. 30, which is a schematic depicting an example of division of an internal tissue 3002 of a patient into regions 3004 for finite element analysis using data obtained by sensing components 3006 located on the boundary of tissue 3002 (e.g., on the skin of the patient), in accordance with some embodiments of the present invention. Each sensing component 3006 is addressable and connected to a controller 3008 via a common barbus 3010, as described herein. There may be n sensing components 3006 and M regions 3004.

Figure 31:
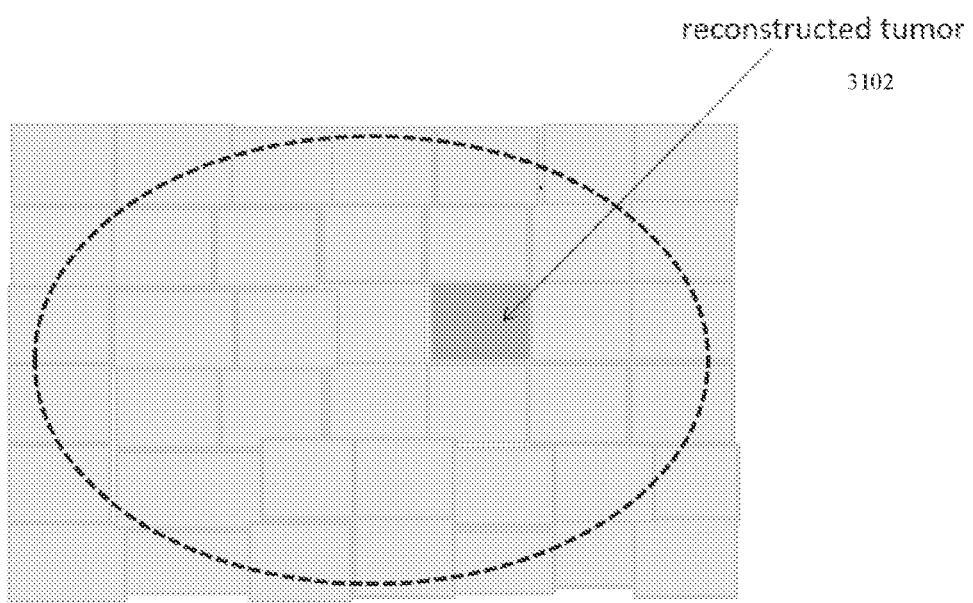
FIG. 31 depicts an exemplary image reconstructed from the impedance dataset, in accordance with some embodiments of the present invention.

Reference is now made to FIG. 31, which depicts an exemplary image reconstructed from the impedance dataset, in accordance with some embodiments of the present invention. Each cell, which may be defined as a single pixel, single voxel, group of pixels (having a common value) and/or a group of voxels (having a common value) is assigned intensity values corresponding to the computed values obtained from the dataset. The generated image may be black and white (e.g., single channel) or color (e.g., multiple channel) created as described herein. A reconstructed tumor 3102 appears at a different intensity in comparison to the other cells denoting normal and/or healthy tissue.

Referring now back to FIG. 3A, at 390, the patient may be diagnosed according to the indication and/or treatment of the patient is planned according to the indication and/or the patient may be treated according to the indication. For example, additional imaging of the patient may be performed using other imaging modalities (e.g., ultrasound, mammogram, CT, MRI), a biopsy may be performed, surgery may be performed, chemotherapy may be administered, radiation therapy may be administered, and/or a watch and wait approach may be selected (e.g., repeat in 1 year).

Referring now back to FIG. 3B, at 310, an arrangement of the sensing components is selected, as described with reference to FIG. 3A.

At 320, the sensing components are placed on the patient, as described with reference to FIG. 3A.

At 321, a calibration may be performed. Calibration may be performed, for example, for different breast sizes and/or for different applications, such as for breast tumor within a breast versus a brain tumor within a brain.

At 322, the sensing components are applied to the surface (e.g., skin) of the body portion of the patient with a uniform pressure, optionally a preselected and/or set pressure. The sensing components may be urged towards to the surface at the uniform pressure.

Contact pressure between the electrodes (of the sensing components) and tissue may affect the impedance measurement. In general, the higher the contact pressure the lower the undesirable contact impedance. A pressure-element (also referred to as a pressure surface) providing uniform contact force of the sensing components to the tissue of the patient may increase accuracy of the generated 3D impedance dataset by reducing variations in measurements resulting from variations in contact pressure, which contribute to impedance mapping error.

The pressure-element coupled to the sensing components includes an urging element set to urge the sensing components for contacting the body portion at the uniform pressure, optionally within a tolerance range. Optionally, the urging element is implemented as a structure (e.g., balloon) that includes a lumen for inflation with a fluid (e.g., saline, water, air). When in use, when the fluid is inserted into the lumen, the lumen expands. In another implementation, springs are implemented. The springs may be preset to apply the uniform pressure.

Optionally, the pressure is applied by a wearable structure that is elastic and set to apply a pressure on the body (e.g., breasts, head) when worn. For example, an external elastic bra worn over a bra like arrangement of the sensing components. In another example, the sensing components are integrated within the elastic wearable garment, that when worn apply pressure to the sensing components towards the skin.

The wearable structure and/or pressure-element may be selected according to size of the body portion.

Figure 32:
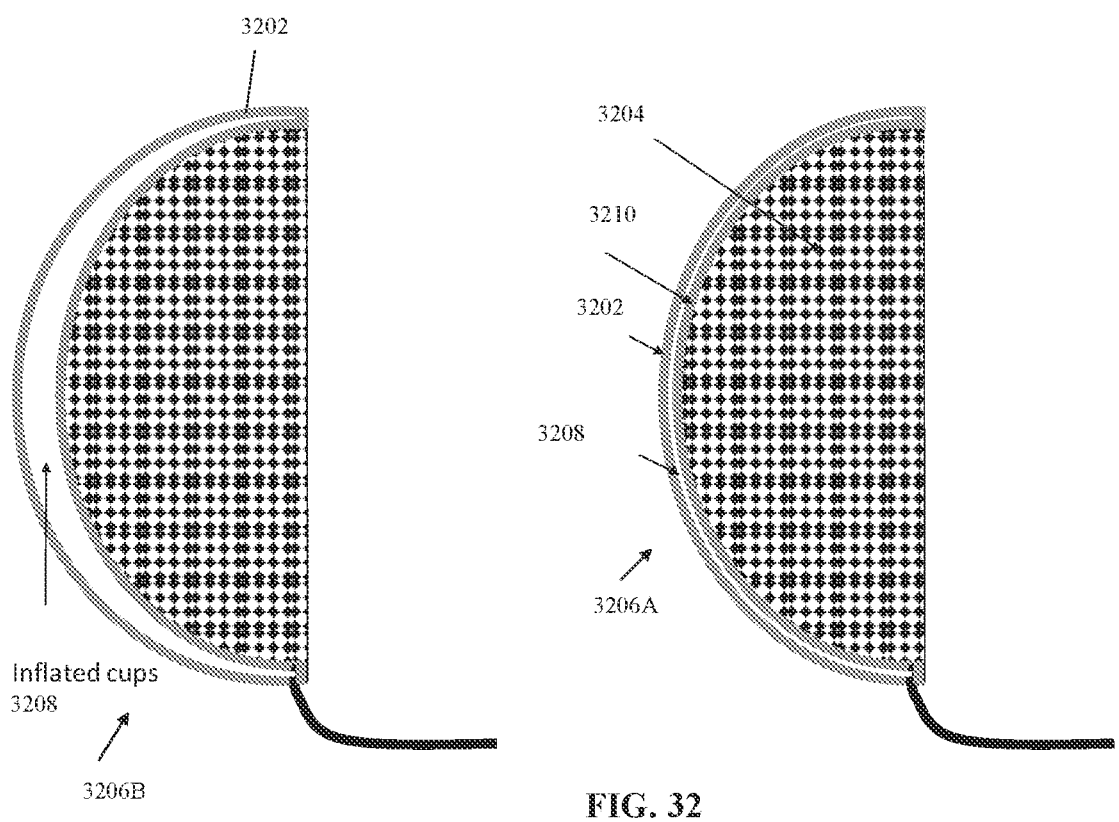
FIG. 32 is a schematic depicting a pressure-element for applying uniform pressure to an array of sensing components contacting tissue of a target patient, in accordance with some embodiments of the present invention.

Reference is now made to FIG. 32, which is a schematic depicting a pressure-element 3202 for applying uniform pressure to an array of sensing components 3204 contacting tissue of a target patient, in accordance with some embodiments of the present invention. Schematic 3206A depicts a lumen 3208 of pressure-element 3202 in an uninflated state. Schematic 3206B depicts lumen 3208 in the inflated state for applying the uniform pressure to sensing components 3204 contacting the tissue. Pressure-element 3202 may be connected to array of sensing components 3204 via support elements 3210 arranged to cup (e.g., encapsulate, at least partially surround) the body portion, as described herein. Lumen 3208 may be inflated to a predefined pressure (e.g., about 75, or 100, or 125 mmHg or other values), and affects (e.g., by Pascal's low equal pressure) all parts of the inner (and/or outer) cup structure shaped pressure-element 3202 reducing or eliminating (e.g., within a tolerance range) the variation in contact impedance due to nonuniform contact force.

Figure 38:
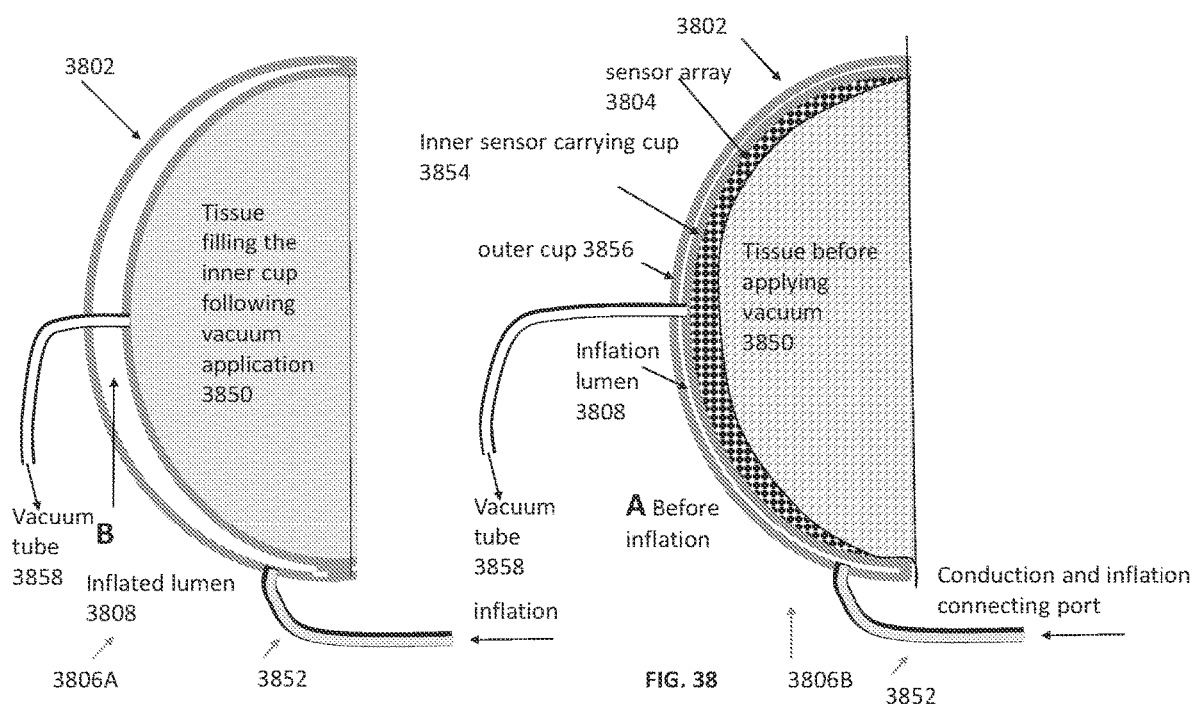
FIG. 38 is a schematic depicting another implementation of a pressure-element designed for application of a vacuum for applying uniform pressure to an array of sensing components contacting a tissue of a target patient, in accordance with some embodiments of the present invention.

Reference is now made to FIG. 38, which is a schematic depicting another implementation of a pressure-element 3802 designed for application of a vacuum for applying uniform pressure to an array of sensing components 3804 (also referred to as sensor array) of a sensing component carrying arrangement (e.g., shaped like a bra) contacting a tissue 3850 (e.g., breast) of a target patient, in accordance with some embodiments of the present invention. It is noted that the applied vacuum and/or non-vacuum is for pressure between the electrodes of the sensing components and the tissue of the body portion of the patient. Schematic 3806A depicts pressure-element 3802 prior to application of the vacuum. An initial pressure may be applied by pressure-element 3802 to sensing components 3804 against tissue 3850, for example, by inflation of lumen 3808 with a fluid (e.g., air, saline, water) optionally via inflation lumen 3852, as described herein (e.g., with respect to FIG. 32), and/or other mechanisms described herein. Lumen 3808 may be located between and/or defined as a space between an inner layer 3854 and an outer layer 3856 of the sensing component carrying arrangement. A vacuum may be applied between the inner layer 3854 of the sensing component carrying arrangement and tissue 3850 via a vacuum tube 3858 connected to a vacuum source (e.g., portable hand pump, home vacuum cleaner). Schematic 3806B depicts pressure-element 3802 when vacuum is being applied (e.g., while the vacuum is being applied and/or after the vacuum has been applied). It is noted that the inflation of the lumen may be performed alone (and/or other non-vacuum pressure may be applied alone), vacuum may be performed along, and/or a combination of the inflation of the lumen (and/or other non-vacuum pressure) and the vacuum may be applied, optionally by first applying the non-vacuum pressure (e.g., inflation of the lumen) followed by application of the vacuum to improve uniform pressure contact between sensor components 3804 and tissue 3850. Optionally, vacuum tube 3858 and inflation port 3852 are connected to the same source, for example, a pump designed to inflate lumen 3808 and in reverse apply the vacuum. Optionally, the controller generates instructions for application of the vacuum and/or inflation fluid. The controller may monitor quality of the contact of the sensing components with the tissue under vacuum and/or inflation, for example, via calibration signals sent between different electrodes. The controller may control the inflation and/or vacuum according to the monitored calibration signals, to obtain a target value indicative of uniform pressure contact between the sensing components and the tissue.

At 330, the controller generates and transmits instructions for sequentially activating a certain sensing component for operating in a selected operation mode, as described with reference to FIG. 3A.

At 340, measurements outputted by the selected sensing component are obtained, as described with reference to FIG. 3A.

At 350, the controller sequentially activates different sensing components and obtains respective measurements from the activated sensing component, by iterating 330 and 340, as described with reference to FIG. 3A. Alternatively, sensing components are automatically sequentially activated in a predefined cascade by circuitry that automatically triggers activation of a subsequently connected sensing component when a current sensing component is selected, such that selection of a first sensing component in a sequence of connected sensing components automatically triggers the sequential independent activation of a next sensing component in the sequence. The automated sequential activation may eliminate and/or reduce the feature of individual addressing of each sensing component, for example, removing the address line from the busbar and/or removing code for addressing from the controller and/or removing the controller and/or simplifying the controller.

Figure 33:
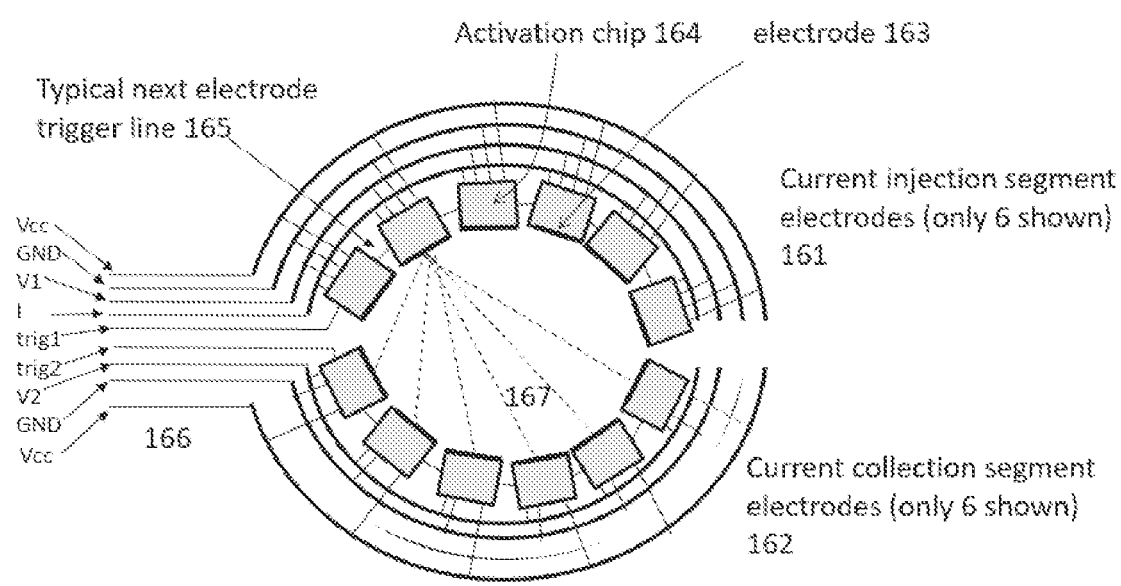
FIG. 33 is a schematic depicting an architecture designed for automated sequential triggering of subsequent sensing components by a currently active sensing component upon termination of activity, in accordance with some embodiments of the present invention.

Reference is now made to FIG. 33, which is a schematic depicting an architecture designed for automated sequential triggering of subsequent sensing components by a currently active sensing component upon termination of activity, in accordance with some embodiments of the present invention. The architecture depicts a slice of sensing components arranged as a circle (e.g., when connected to a support element shaped as the circle). Sensing components (which include electrodes as described herein) are arranged as a semicircle of current injecting electrodes 161 and a complementary semicircle of collecting electrodes 162. Each electrode 163 is attached to a drive/measurement chip 164. A connecting busbar 166 incorporates the following lines: DC, GND, V1, I (current injection line), trig1, trig2 and V2.

As described herein, when triggered the electrode injects a known current drawn from the I line into the tissue. The current is collected by the counter electrode as indicated by one of the broken lines 167. The voltage drop is sensed and delivered via lines V1 and V2 to an amplifier and next to the controller.

It is noted that each of the injecting electrodes current is collected by all collecting electrodes one at a time before the next injecting electrode is triggered.

Figure 34:
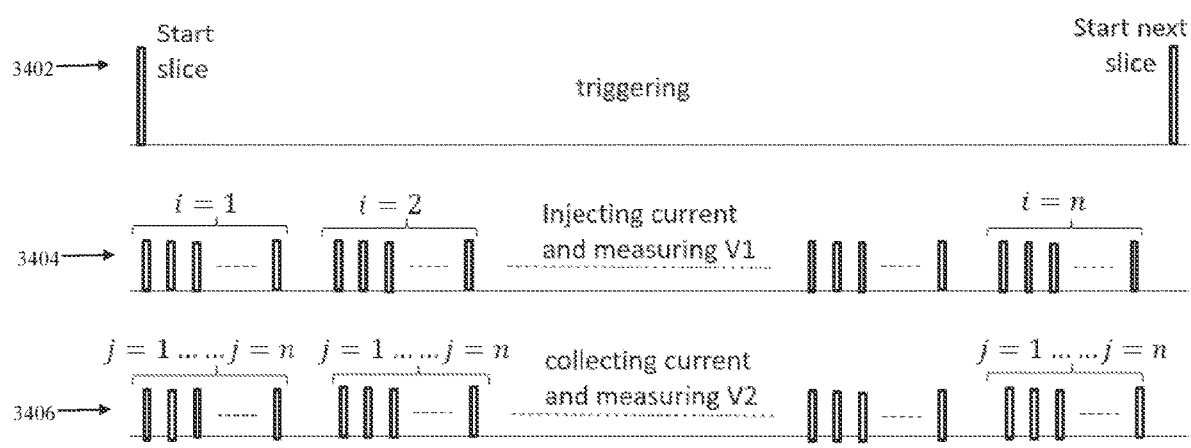
FIG. 34 is a schematic of a timing diagram for generating instructions for operation of the architecture of FIG. 33, in accordance with some embodiments of the present invention.

Reference is now made to FIG. 34, which is a schematic of a timing diagram for generating instructions for operation of the architecture of FIG. 33, in accordance with some embodiments of the present invention. Timing diagram 3402 depicts that each slice cycle stats with a trigger that activate the first electrode. Timing diagram 3404 depicts that the currently activated electrode injects a train of n current pulses each collected by a different receiving electrode as depicted in timing diagram 3406. Each of the collecting electrodes triggers the next electrode. Once the first set of collecting electrodes has been completed the next injection electrode is triggered again injecting a train of n pulses collected by the n receiving electrodes. The process continues until all injecting electrodes have been activated. It should be noted that instead of one electrode driver switching from one electrode driver to the next, special switching lines (not shown) may be used (similar to a shift register) to perform the switching from chip to chip on both injection section 161 and collecting section 162.

At the end of the slice cycle the processor possesses all $n^2$ measurements denoted $R_{i,j}$ that are used for computing the impedance dataset (e.g., 3D dataset), as describe herein.

It is noted that the driver chip does not necessarily require to have an address decoder. When triggered the driver chip performs a set of n injections followed by triggering of the next chip until the slice cycle has completed.

Figure 35A:
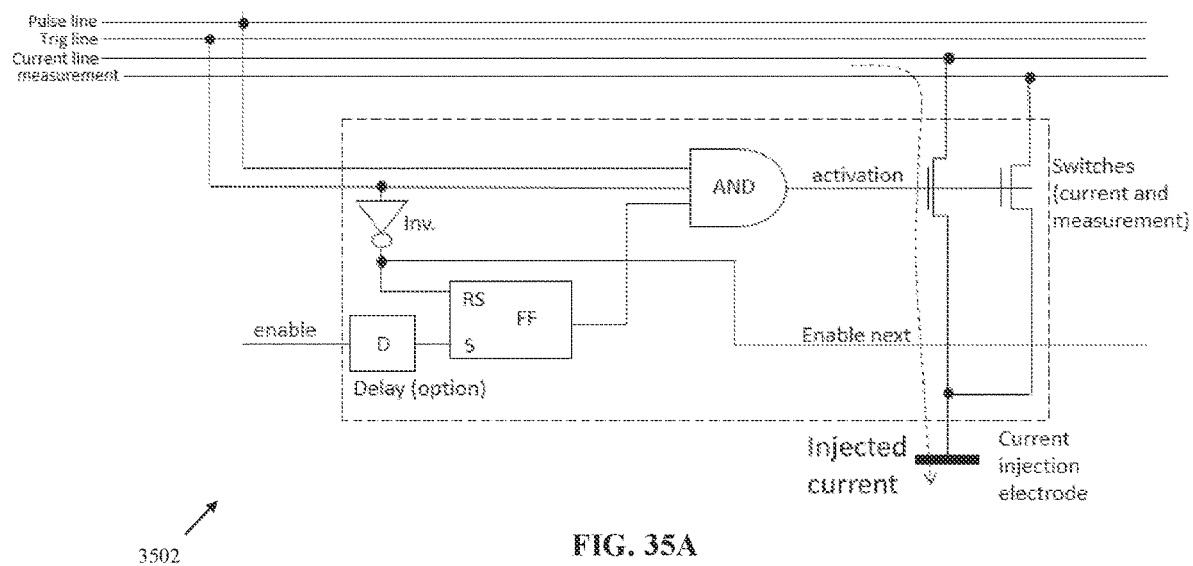
FIGS. 35A-B are a schematic of an exemplary circuit diagram of a chip including a sensing component designed for automatic triggering of a next sensing component upon termination of activity of activity of the current sensing component, in accordance with some embodiments of the present invention.
Figure 35B:
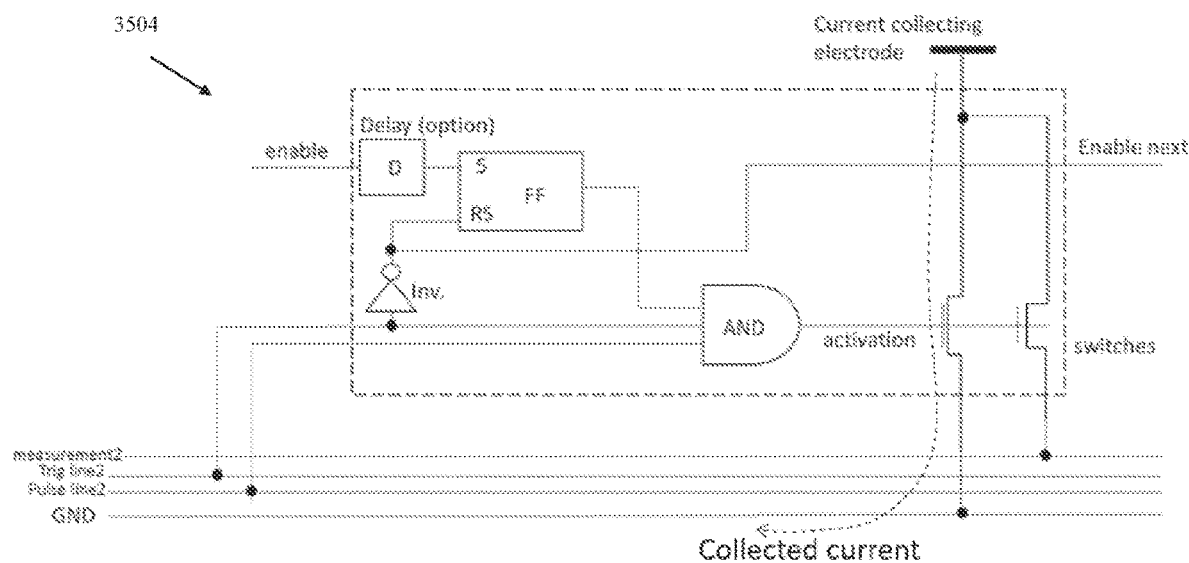

Reference is now made to FIGS. 35A-B, which are a schematic of an exemplary circuit diagram of a chip 3502 3504 including a sensing component designed for automatic triggering of a next sensing component upon termination of activity of activity of the current sensing component, in accordance with some embodiments of the present invention. Chip 3502 3504 may be part of the architecture described with reference to FIG. 33. Chip 3502 (i.e., sensing component) is operated as a current injector in FIG. 35A. Chip 3504 (i.e., sensing component) is operated as a current collector in FIG. 35B. Each chip 3502 3504 receives logic operating commands as well as an enable command from the prior chip since they operate sequentially. When the chip gets all its inputs as high the output switches the current and the measurement on the current injection strip section and simultaneously the current collecting strip section is activated sequentially. It is noted that each injection electrode may feeds sequentially all collecting electrodes. For n injection electrodes and m collecting electrodes a n×m measurement dataset is acquired (e.g., for each slice).

Figure 36:
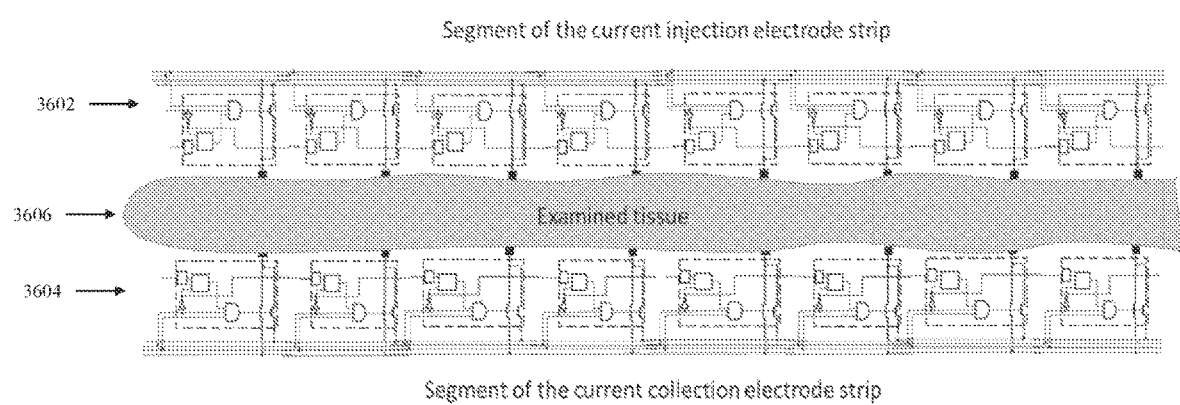
FIG. 36 is a schematic depicting a sequence of eight chips of sensing components designed to operate as current injectors and another sequence of eight chips of sensing components designed to operate as current collectors for collecting an impedance dataset of a target tissue, in accordance with some embodiments of the present invention.

Reference is now made to FIG. 36, which is a schematic depicting a sequence of eight chips 3602 of sensing components designed to operate as current injectors and another sequence of eight chips 3604 of sensing components designed to operate as current collectors for collecting an impedance dataset of a target tissue 3606, in accordance with some embodiments of the present invention. Current injector chips 3602 are depicted with reference to FIG. 35A. Current collector chips 3604 are depicted with reference to FIG. 35B. The circuitry depicted in FIG. 36 may be fabricated on a chip as an FPGA and/or an ASIC. The chips may be mounted on one side the flex PCB creating a contact with the conducting lines. The electrode is optionally mounted on the other side of the strip.

Referring now back to FIG. 3B, at 352, the controller may activate each pair of the current source and current sink and the other sensing components as the respective voltage sensor multiple times (e.g., three times) for obtaining multiple sets of voltage readings each at a different frequency of the current. Changing the current frequency may provide different information when the tissue impedance being measured is a complex value dependent on frequency.

The multiple frequencies may be used for designating a respective color channel for each one of the three sets of voltage readings corresponding to a different frequency. The 3D image and/or 3D dataset may be generated in color using the respective color channels. For example, when 3 different frequencies are used, a synthetic color image may be reconstructed, for example, red green blue (RGB), by assigning a different color to each frequency.

At 354, other sensors are sequentially activated.

Optionally, the other sensors are each located in proximity to at least some of the sensing components. Optionally, the other sensors are connected to the busbar. Each pair of another sensor and the sensing component may share a single unique address. Another instruction (e.g., transmitted via a dedicated line component of the busbar) may instruct activation and/or operation of the sensing component or the other sensor. The controller may be arranged to sequentially independently activate at a time, each respective other sensor, for collecting measurements from the multiple other sensors for generating a 3D dataset and/or 3D image of the body portion based on the other sensor measurements.

The other sensor may be, for example, an infra-red (IR) sensor.

Alternatively, or additionally, at least a subset of the sensing components are designed to further operate in ultrasound mode. The ultrasound sensors and sensing components may be spatially congruent. The sensing components designed for ultrasound each include a tissue electrode for contacting the body portion, a second electrode in parallel with the tissue electrode, and an ultrasonic element (e.g., piezoelectric) sandwiched between the tissue electrode and the second electrode. The tissue element may be selectively activated as the current source, the current sink or the voltage sensor (as described herein). In an ultrasound mode, the tissue electrode, the ultrasound element, and the second electrode are activated as an ultrasound transducer for obtaining ultrasound measurements, for generation of an ultrasound dataset and/or ultrasound image (e.g., 2D and/or 3D image).

Optionally, first, all sensors of a first type are activated for obtaining a 3D dataset of the first type (e.g., IR, ultrasound, impedance). The 3D dataset of the first type may be used to instruct the sensors of the second type, for obtaining improved measurements, for example, the location of the tumor may be first found in the 3D dataset of the first type, and the sensors of the second type activated to provide improved imaging of the tumor in the 3D dataset of the second type.

Figure 37:
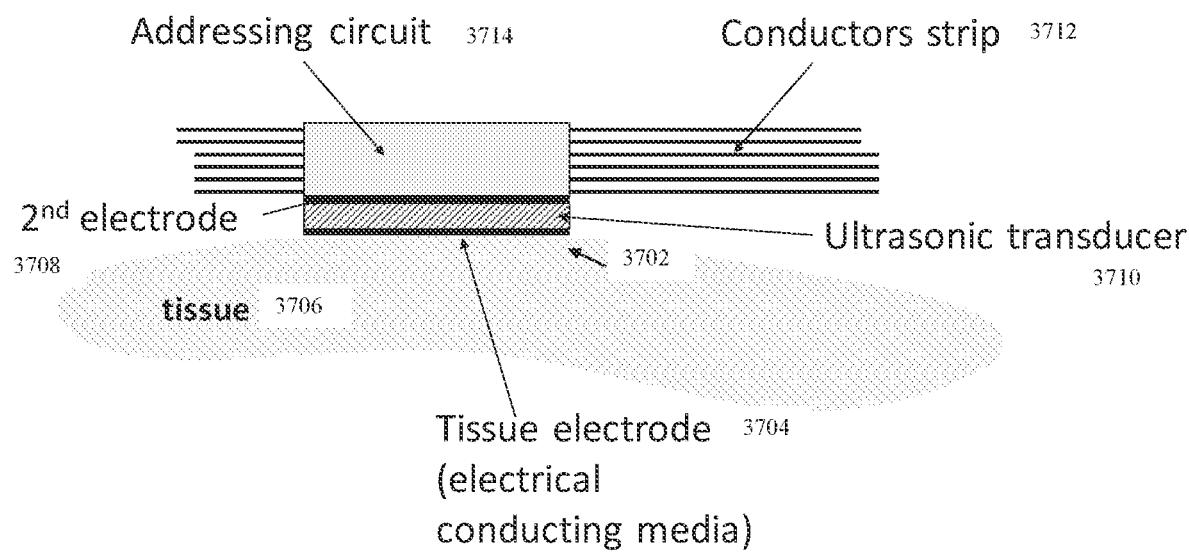
FIG. 37 is a schematic of a design of a combination sensing component that is operable as an electrode for measuring impedance (e.g. current and/or voltage) and as an ultrasound transducer for obtaining ultrasound data, in accordance with some embodiments of the present invention.

Reference is now made to FIG. 37, which is a schematic of a design of a combination sensing component 3702 that is operable as an electrode for measuring impedance (e.g. current and/or voltage) and as an ultrasound transducer for obtaining ultrasound data, in accordance with some embodiments of the present invention. Combination sensing component 3702 includes a tissue electrode 3704 for contacting tissue 3706 that may serve as an ultrasound transducer and/or electrode for measuring impedance (e.g., current and/or voltage). Combination sensing component 3702 includes a second electrode 3708 positioned in parallel to tissue electrode 3704 and a piezoelectric element sandwiched between electrodes 3704 and 3706 for creation of an ultrasound transducer 3710. Combination sensing component 3702 may be connected to a busbar 3712 and addressable via an addressing circuit 3714, as described herein. Combination sensing component 3702 may include circuitry that identifies the follow instructions generated by the controller and transmitted via busbar 3712: its unique address on, mode of operation (e.g., impedance, ultrasound, current source, current sink, voltage sensor), and circuitry for activating switches to operate in the mode of operation when the unique address id detected.

At 356, measurements outputted by the other sensors are obtained.

At 358, features 354 and 356 are iterated for sequentially activating at least some of the other sensors for obtain respective measurements, which are provided for generating a 3D dataset and/or image based on the other sensor measurements.

At 360, the obtained sets of measured currents and voltages and/or impedance values, optionally for each pair of current source and current sink, are provided for further computation and/or analysis, as described with reference to FIG. 3A. Optionally, measurements obtained from the other sensors (e.g., IR, ultrasound) are provided.

At 370, a 3D dataset of impedance values of the body portion is computed from the measured current, voltage, and/or impedance values, as described with reference to FIG. 3A. Optionally, another 3D dataset is computed from the other sensor measurements (e.g., IR, ultrasound).

Alternatively, or additionally, other 3D datasets obtained from other imaging modalities are obtained, for example, CT, MRI, nuclear medicine scan (e.g., PET).

At 372, the 3D dataset of impedance values is correlated with the 3D dataset of other sensor measurements and/or with the 3D dataset of other imaging modalities and/or with other 3D datasets obtained from other imaging modalities. The correlation of multiple datasets may increase accuracy of detection of the malignancy, as described herein.

At 380, the 3D dataset and/or the correlated 3D dataset is analyzed, and/or a correlated 3D image of the body portion may be generated, for presentation, analysis, and/or storage, as described with reference to FIG. 3A.

At 390, the patient may be diagnosed according to the indication and/or treatment of the patient is planned according to the indication and/or the patient may be treated according to the indication, as described with reference to FIG. 3A.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant sensing components will be developed and the scope of the term sensing component is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety.

What is claimed is:

1. A system for mixed imaging modalities including impedance based analysis of a body portion of a patient, comprising:
    at least one multi conductor busbar, each bus bar of the at least one multi conductor busbar is connected to a controller and at least two of a plurality of sensing circuitries;
    a controller arranged to:
        activate in each of a plurality of iterations:
        operating a pair of first and second sensing circuitries from the plurality of sensing circuitries, the pair of the first and second sensing circuitries have not been selected in previous iterations of the plurality of iterations,
            the first sensing circuitry is activated as a current source and the second sensing circuitry is sequentially activated as a current sink,
            obtaining a plurality of surface voltages while alternating current (AC) is transmitted between the first and second sensing circuitries, by sequentially activating sensing circuitries from the plurality of sensing circuitries which are not the first and second sensing circuitries as a voltage sensor,
        the plurality of surface voltages and current obtained in each of the plurality of iterations are provided for computation of a three dimensional (3D) dataset of 3D impedance values of the body portion, provided for analysis thereof; and
    at least one hardware processor for generating an impedance based intra-body conductivity mapping image of the body portion from the 3D dataset.

2. The system of claim 1, wherein the controller performs sequentially activating each of the first and second sensing circuitries by transmitting a unique address associated therewith on the at least one multi busbar.

3. The system of claim 1, wherein each of the plurality of sensing circuitries includes:
    (i) an address decoder that is activated when a unique address is transmitted over the at least one multi conductor busbar;
    (ii) at least one electrode for contacting tissue;
    (iii) at least one switch that connects the at least one electrode to a busbar from the at least one multi conductor busbar when the address decoder is activated by the unique address; and
    (iv) an assignment mode decoder that receives instructions from the busbar from the at least one multi conductor busbar for selectively operating the at least one electrode as a current source, as a current sink, or as a voltage sensor, when the address decoder is activated by the unique address.

4. The system of claim 3, wherein each of the of the plurality of sensing circuitries further includes an amplifier for amplifying the voltage reading obtained by the at least one electrode when the assignment mode decoder operates the at least one electrode as the voltage sensor.

5. The system of claim 3, wherein the at least busbar includes the following busbar components: a transmit current circuitry for transmission of current for operating one of the plurality of sensing circuitries as a current source, a receive current circuitries operating as current mode, a ground circuitry denoting ground, at least one voltage circuitry for transmission of sensed voltage from at least one voltage sensor, and an address circuitry for transmission of the unique address and a clocking circuitry.

6. The system of claim 1, further comprising a pressure-surface coupled to the plurality of sensing circuitries, the pressure-surface includes an urging element set to urge the plurality of sensing circuitries for contacting the body portion at a uniform pressure within a tolerance.

7. The system of claim 1, wherein the at least one hardware processor is adapted for: computing a computational model of the 3D dataset of impedance values, matching the voltages obtained for each pair of current source and current sink during the plurality of iterations to computed boundary values obtained by the computational model including Laplace's equation incorporating distributed conductivity, and iteratively adjusting the computational model including the conductivity distribution until the obtained voltages and currents match the computed boundary values within an error range.

8. The system of claim 7, wherein an initial set of conductivity distribution values of the computational model of the 3D dataset is obtained by the controller sequentially activating the first and second circuitries from the plurality of sensing circuitries, and obtaining voltage readings from the first and second circuitries while current is flowing therebetween.

9. The system of claim 1, wherein the analysis of the body portion, by conductivity distribution mapping for tissue anomaly observation, is for planning treatment of the patient.

10. The system of claim 1, wherein the body portion comprises one or two breasts, and the plurality of sensing circuitries are arranged as a bra for cupping the one or two breasts.

11. The system of claim 1, further comprising a plurality of support elements arranged for contacting and at least partially cupping the body portion of the patient, wherein the at least one multi conductor busbar and the plurality of sensing circuitries are coupled to the plurality of support elements; wherein the plurality of support elements are arranged in a partial or full ring arrangement for encompassing at least a region of the body portion of the patient; wherein each support element of the plurality of support elements includes a single busbar for connecting to at least two sensing circuitries of the plurality of sensing circuitries which are coupled to the support element and for connecting to the controller.

12. The system of claim 11, wherein the plurality of support elements are arranged as extensions from a common region of the cup arrangement, wherein each extension of the extensions curves out from the common region; wherein the plurality of sensing circuitries are automatically and sequentially activated in a predefined cascade such that selection of the first sensing circuitry automatically triggers a sequential independent activation of a next sensing circuitry in the sequence.

13. The system of claim 1, further comprising code for segmenting tissue indicative of likelihood of malignancy depicted in the impedance based intra-body 3D conductivity mapping image.

14. The system of claim 13, wherein the segmenting is performed by a machine learning model trained on a training dataset of a plurality of 3D conductivity images obtained from a plurality of sample patients.

15. The system of claim 1, wherein in each of the plurality of iterations the controller activates the sensing circuitries from the plurality of sensing circuitries which are not the first and second sensing circuitries as the voltage sensor three times for obtaining a plurality of sets of voltage readings each at a different frequency of the current, for designating a color channel for each one of the plurality of sets of voltage readings corresponding to a different frequency, and wherein the impedance based intra-body 3D conductivity mapping image is generated in color using the color channels.

16. The system of claim 1, wherein the controller is further designed to sequentially activate in ultrasound mode, at least some of the sensing circuitries, obtain a ultrasound measurement, and provide a plurality of ultrasound measurements for generating at least one of: a 3D ultrasound intra-body image of the body portion, and conductivity mapping; wherein the at least one hardware processor is adapted for correlating the 3D dataset of impedance values with the plurality of ultrasound measurements, and generating a correlated 3D image of the body portion based on the plurality of ultrasound measurements.

17. The system of claim 1, wherein at least a subset of the plurality of sensing circuitries are designed further operate in ultrasound mode, by each including a tissue electrode for contacting the body portion, a second electrode in parallel with the tissue electrode, and an ultrasonic element sandwiched between the tissue electrode and the second electrode, wherein the tissue element is selectively activated as the current source, the current sink or the voltage sensor, and in an ultrasound mode the tissue electrode, the ultrasound element, and the second electrode are activated as an ultrasound transducer.

18. The system of claim 1, wherein the at least one multi conductor busbar includes at least one of:
    (i) a master busbar connected to the plurality of sensing circuitries arranged in a substantially circular arrangement via a plurality of branching sub-busbars;
    (ii) a single continuous busbar with a staggered designed; and
    (iii) a single continuous busbar connecting the plurality of sensing circuitries along a spiral arrangement.

19. The system of claim 1, wherein a plurality of electrodes are arranged along a long axis of each support element of a plurality of support elements, each of the plurality of electrodes including an individual conductor connected to a main busbar connector designed to connect to the at least one multi conductor busbar, wherein addressing circuitry and switching circuitry for sequential activation of the plurality of electrodes is located in association with the main busbar connector, which the plurality of support elements are arranged in a fan arrangement designed for being shaped into a cup like arrangement for cupping the body portion.

20. The system of claim 1, wherein the at least one multi conductor busbar comprises less than 10 conductors.

21. The system of claim 1, wherein the intra-body conductivity mapping image comprises one or more two dimensional (2D) parallel slices.

22. A method of an impedance based analysis of a body portion of a patient, comprising:
    providing at least one multi conductor busbar connecting a plurality of sensing electrodes, each bus bar of the at least one multi conductor busbar is connected to a controller and to at least two of the plurality of sensing electrodes;
    iteratively performing:
        sequentially activating as a pair of current electrodes from the plurality of sensing electrodes at a time,
        wherein a plurality of voltages and current obtained for each pair of current electrodes of each iteration are provided for computation of a three dimensional (3D) dataset of impedance values of the body portion, provided for analysis thereof;
    providing at least one hardware processor for generating an impedance based intra-body conductivity mapping image of the body portion from the 3D dataset.

* * * * *